(12) United States Patent (10) Patent No.: US 12,571,734 B2

Kim et al. (45) Date of Patent: Mar. 10, 2026

(54) DEVICE AND METHOD FOR DETECTING LIGHT

(71) Applicant: SEEGENE, INC., Seoul (KR)

(72) Inventors: Young Wook Kim, Seoul (KR); Jun Hyeok Jeong, Seoul (KR); Hye Jin Lee, Anyang-si (KR)

(73) Assignee: SEEGENE, INC., Seoul (KR)

( * ) Notice: Subject to any disclaimer, the term of this patent is extended or adjusted under 35 U.S.C. 154(b) by 1135 days.

(21) Appl. No.: 17/614,740

(22) PCT Filed: May 29, 2020

(86) PCT No.: PCT/KR2020/007044
§ 371 (c)(1),
(2) Date: Nov. 29, 2021

(87) PCT Pub. No.: WO2020/242263
PCT Pub. Date: Dec. 3, 2020

(65) Prior Publication Data
US 2022/0228988 A1    Jul. 21, 2022

(30) Foreign Application Priority Data

| | | |
|---|---|---|
| May 31, 2019 | (KR) | 10-2019-0064472 |
| Jun. 28, 2019 | (KR) | 10-2019-0078284 |
| Dec. 6, 2019 | (KR) | 10-2019-0162094 |

(51) Int. Cl.
*G01N 21/64* (2006.01)
*B01L 3/00* (2006.01)
(Continued)

(52) U.S. Cl.
CPC ...... *G01N 21/6452* (2013.01); *B01L 3/50851* (2013.01); *C12Q 1/686* (2013.01);
(Continued)

(58) Field of Classification Search
CPC .... G01N 21/6452; G01N 21/01; G01N 21/64; G01N 21/6408; G01N 21/6428;
(Continued)

(56) References Cited

U.S. PATENT DOCUMENTS 9,244,014 B2   1/2016  Kim et al.
2009/0068747 A1   3/2009  Iten
(Continued)

FOREIGN PATENT DOCUMENTS

CN    207742096 U    8/2018
JP    2003344290 A    12/2003
(Continued)

OTHER PUBLICATIONS

Office Action for corresponding Korean Patent Application No. 10-2021-7042113 dated Dec. 22, 2023, with English translation (20 Pages).
(Continued)

*Primary Examiner* — Huy Tram Nguyen

(74) *Attorney, Agent, or Firm* — Harness, Dickey & Pierce, P.L.C.

(57) ABSTRACT

Embodiments of the disclosure relate to a device and method for detecting light in a plurality of independent reaction regions. According to the disclosure, a light detection device includes a plurality of thermally independent reaction regions, a movable optical module for irradiating the reaction regions with lights of a plurality of wavelengths, detectors for detecting lights emitted from the reaction regions, and a controller controlling the reaction regions, the optical module, and the detectors.

12 Claims, 9 Drawing Sheets

(51) Int. Cl.
    *C12Q 1/686*     (2018.01)
    *G01N 21/01*     (2006.01)

(52) U.S. Cl.
    CPC ............. *G01N 21/01* (2013.01); *G01N 21/64* (2013.01); *G01N 21/6408* (2013.01); *G01N 21/6428* (2013.01); *B01L 2300/0663* (2013.01); *B01L 2300/1822* (2013.01); *B01L 2300/1827* (2013.01); *G01N 2021/6417* (2013.01); *G01N 2021/6421* (2013.01); *G01N 2021/6439* (2013.01); *G01N 2021/6441* (2013.01)

(58) Field of Classification Search
    CPC ... G01N 2021/6417; G01N 2021/6421; G01N 2021/6439; G01N 2021/6441; G01N 2021/6463; G01N 2021/6419; G01N 2021/6471; G01N 2021/745; B01L 3/50851; B01L 2300/0663; B01L 2300/1822; B01L 2300/1827; B01L 2200/0663; B01L 7/52; B01L 2300/0627; C12Q 1/686; C12Q 1/6816; C12Q 2537/143; C12Q 2561/113; C12Q 2563/107
    USPC ......................................................... 422/109
    See application file for complete search history.

(56) References Cited

U.S. PATENT DOCUMENTS

| | | |
|---|---|---|
| 2011/0312102 A1 | 12/2011 | Jo |
| 2012/0064534 A1 | 3/2012 | Pipper et al. |
| 2013/0143308 A1 | 6/2013 | Kordunsky et al. |
| 2014/0045186 A1 | 2/2014 | Gubatayao et al. |
| 2016/0282268 A1 | 9/2016 | Morimoto et al. |
| 2017/0130261 A1 | 5/2017 | Nagai et al. |
| 2018/0258465 A1 | 9/2018 | Wang |

FOREIGN PATENT DOCUMENTS

| | | |
|---|---|---|
| JP | 2015006203 A | 1/2015 |
| KR | 1020120116778 A | 10/2012 |
| KR | 1020120139206 A | 12/2012 |
| KR | 2013-0071645 A | 7/2013 |
| KR | 1020130071645 A | 7/2013 |
| KR | 20150094811 A | 8/2015 |

OTHER PUBLICATIONS

Office Action for corresponding Korean Patent Application No. 10-2021-7042113 dated Jan. 22, 2025, with English translation (9 Pages).

Office Action for corresponding Korean Patent Application No. 10-2021-7042916 dated Nov. 30, 2023, with English translation (18 Pages).

Office Action for corresponding Korean Patent Application No. 10-2021-7042916 dated Dec. 13, 2024, with English translation (8 Pages).

Extended European Search Report for corresponding European Patent Application No. 20812735.7 dated Dec. 19, 2022 (9 Pages).

Office Action for corresponding European Patent Application No. 20812735.7 dated Jun. 26, 2024 (9 Pages).

International Search Report and Written Opinion of the ISA issued in PCT/KR2020/007044, mailed Sep. 4, 2020; ISA/KR.

DEVICE AND METHOD FOR DETECTING LIGHT

CROSS-REFERENCE TO RELATED APPLICATIONS

This application is a U.S. National Phase Application under 35 U.S.C. 371 of International Application No. PCT/KR2020/007044, filed on May 29, 2020, which claims the benefit of Korean Patent Application No. 10-2019-0064472, filed on May 31, 2019, Korean Patent Application No. 10-2019-0078284, filed on Jun. 28, 2019, and Korean Patent Application No. 10-2019-0162094, filed on Dec. 6, 2019. The entire disclosures of the above application are incorporated herein by reference in their entirety.

TECHNICAL FIELD

Embodiments of the disclosure relate to a device and method for detecting light in a plurality of independent reaction regions.

BACKGROUND ART

Nucleic acid amplification reaction well known as polynucleotide chain reaction (PCR) includes repeated cycles of doube-stranded DNA denaturation, annealing of the oligonucleotide primers to DNA templates, and extension/elongation of the primers with the DNA polymerase (Mullis et al., U.S. Pat. Nos. 4,683,195, 4,683,202, and 4,800,159; Saiki et al., (1985) Science 230, 1350-1354). DNA denaturation is performed at about 95° C., and anealing and primer elongation are performed at a lower temperature ranging frm 55° C. to 75° C.

Real-time PCR is a method for real-time monitoring amplification of a target nucleic acid sequence using a label or a labeled oligonucleotide that may emit fluorescence dependently upon the target nucleic acid sequence.

Typically, a real-time PCR device includes a light source that radiates excitation light to the reaction region or sample and a detector for detecting light emitted from the light source and sample.

In PCR using a PCR device having a plurality of heating blocks thermally independent from each other, an independent reaction protocol may be performed per heating block. To real-time monitor the reaction performed in each heating block, it is required to illuminate each heating block with light and detect the light emitted from the heating block.

In PCR using a PCR device having a plurality of heating blocks thermally independent from each other, each heating block may be illuminated at a different time. Or, the heating blocks may be illuminated at the same time.

A need exists for a more efficient device capable of receiving multiple samples in a plurality of heating blocks thermally independent from each other and detecting the presence of a plurality of target nucleic acid sequences.

Several patents and documents are cited herein. The disclosures of such patents and documents are incorporated by reference herein in their entireties to clearly describe the prior art.

DISCLOSURE OF INVENTION

Technical Problem

Embodiments of the disclosure relate to a device and method for detecting light in a plurality of thermally independent reaction regions.

Accordingly, it is a purpose of the present disclosure to provide a light detection device.

It is another purpose of the present disclosure to provide a method for detecting light.

It is still another purpose of the present disclosure to provide to provide a computer readable storage medium comprising instructions stored therein, wherein the instructions are configured to enable a processor of the computer to perform a method for detecting light.

Solution to Problem

To achieve the foregoing purpose, according to one aspect of the disclosure, there is provided a light detection device comprising: thermally independent reaction regions, wherein the reaction regions are capable of receiving one or more samples, and temperatures of the reaction regions is controlled indepndently, light source units irradiating the reaction regions with light, wherein the light source units comprising two or more light source units radiating different lights, and each of the light source units irradiate an area of predetermined size with light, wherein the light source units are configured to be movable; one or more controller controlling the temperatures of the reaction regions independently and controlling movement of the light source units, and detectors detecting light emitted from the reaction regions.

According to an embodiment, each of the reaction regions comprises wells arranged in an n×m matrix, and wherein n or m is a natural number which is two or more.

According to an embodiment, one of the light source units irradiates one entire reaction region with the light, or two or more light source units separately irradiate one entire reaction region with the light.

According to an embodiment, two of the light source units separately irradiate one entire reaction region with the light by deviding the one entire reaction region.

According to an embodiment, the light source units are simultaneously moved, and wherein areas irradiated with the light by the light source units are simultaneously changed.

According to an embodiment, the light source units are arranged around a rotational axis, and wherein as the light source units are rotated around the rotational axis, areas irradiated with the light by the light source units are changed.

According to an embodiment, the light source units are rotated around the rotational axis at 90 degrees, 180 degrees, 270 degrees, or 360 degrees.

According to an embodiment, the light source units are linearly arranged, and wherein as the light source units are simultaneously moved along a straight line, areas irradiated with the light are changed.

According to an embodiment, the light source units radiate, at least one once, the light to a reaction region reaching a light detection time among the reaction regions.

According to an embodiment, at least one of the light source units is positioned in one reaction region, and at least one other light source unit is positioned in another reaction region so that different reaction regions may be synchronously irradiated with different lights.

According to an embodiment, each of the light source units comprises one or more light sources.

According to an embodiment, the light source units comprise four or more light source units capable of radiating four or more different lights.

According to an embodiment, the reaction regions comprise a first reaction region and a second reaction region, wherein the light source units comprise a first light source unit and a second light source unit, and wherein when the first reaction region and the second reaction region simultaneously reach a light detection time, as the light source units are rotated, the first light source unit is positioned in the first reaction region, and the second light source unit is positioned in the second reaction region to synchronously irradiate different areas with different lights.

According to an embodiment, one or more detectors are disposed for one reaction region.

According to an embodiment, one detector is disposed for an area irradiated with the light by one light source unit in one reaction region.

According to an embodiment, one or more different detectors of the detectors are assigned to each of the reaction regions, and wherein light emitted from each reaction region is measured by the one or more different detectors assigned.

According to an embodiment, the controller may independently control on/off of light irradiation of the light source units.

According to another aspect of the sidclosure, there is provided a method for detecting light, the method comprising: independently controlling temperatures of thermally independent reaction regions, wherein the reaction regions are capable of receiving one or more samples; positioning light source units in reaction regions reaching a light detection time among the reaction regions and irradiating the reaction regions with light, wherein the light source units are configured to be movable and comprising two or more light source units radiating different lights, and each of the light source units irradiate an area of predetermined size with light; and detecting light emitted from the reaction regions.

According to another aspect of the sidclosure, there is provided a computer readable storage medium comprising instructions stored therein, wherein when the instructions is executed by a computer, the instructions are configured to enable a processor of the computer to perform a method for detecting light, the method comprising: independently controlling temperatures of thermally independent reaction regions, wherein the reaction regions are capable of receiving one or more samples; positioning light source units in reaction regions reaching a light detection time among the reaction regions and irradiating the reaction regions with light, wherein the light source units are configured to be movable and comprising two or more light source units radiating different lights, and each of the light source units irradiate an area of predetermined size with light; and detecting light emitted from the reaction regions.

Advantageous Effects of Invention

According to the disclosure, the temperature of thermally independent reaction regions may be independently controlled, and reaction regions, which reach a detection temperature, may be efficiently illuminated with light.

According to the disclosure, two or more reaction regions may be synchronously or asynchronously irradiated with light by moving one optical module, rather than individually using optical modules comprising a plurality of light source groups per reaction region.

According to the disclosure, one light source unit or two light source units are configured to irradiate one entire reaction region with light, thereby minimizing the steps of moving the optical module.

According to the disclosure, the rotational optical module is more useful for synchronously or individually radiating a plurality of lights to a plurality of adjacent reaction regions.

According to the disclosure, the region where samples are received is partitioned into sections so that a plurality of light source units and detectors perform light detection in their respective predetermined sections. As compared with detection devices which simultaneously sense emission lights from all samples using a single detector, the device according to the disclosure has a relatively small region as detected by each detector. Thus, the sample and the detection unit may be configured to be closer to each other, and this enables detection of optic signals of a smaller amount of light and reduction in inter-sample signal deviation.

Further, even when different optic signals from the samples received in two or more reaction regions are simultaneously measured using detectors controlled independently controlled per thermally independent reaction region, precise detection may be performed without signal interference.

MODE FOR THE INVENTION

The configuration and effects of the disclosure are now described in further detail in connection with embodiments thereof. The embodiments are provided merely to specifically describe the disclosure, and it is obvious to one of ordinary skill in the art that the scope of the disclosure is not limited to the embodiments.

Figure 1:
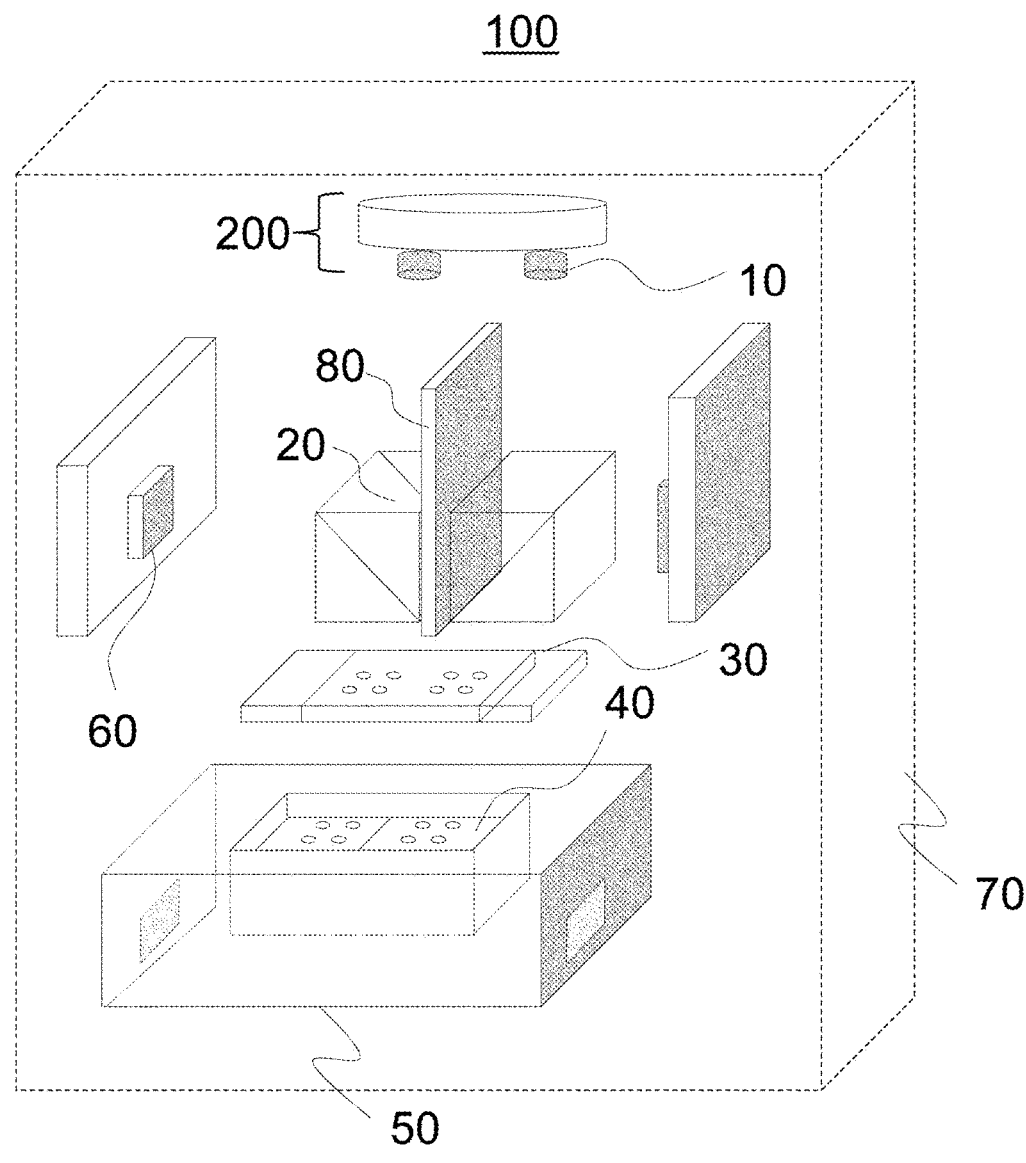
FIG. 1 is a view illustrating a light detection device according to an embodiment of the disclosure.

FIG. 1 is a view illustrating a light detection 100 device according to an embodiment of the disclosure. Referring to FIG. 1, the light detection device 100 includes an optical module 200 including two light source units 10, two beam splitters 20, and two reaction regions 40. Referring to FIG. 1, a light detection device 100 includes an optical module 200, a beam splitter 20, a pressure lid 30, reaction regions 40, a heating block housing 50, a detector 60, and a case 70.

The light detection device 100 is a device for detecting optic signals from samples. According to an embodiment, the signals may be signals indicating the presence of a target analyte, particularly, a target nucleic acid, in the samples. Thus, the device according to the disclosure may be an optic signal detection device or target nucleic acid detection device.

Reaction region means a physical space where a reaction or experiment for a sample is performed. According to the disclosure, the reaction region may individually receive a plurality of samples and may be structured to be able to transfer heat to the sample when reaction for the sample proceeds and to allow the sample and the device to optically communicate with each other to be able to perform light detection.

The reaction regions 40 may be elements that may receive one or more samples and heat or cool the samples. The reaction region may also be referred to as a reaction element.

The reaction region 40 may have a space that may directly receive a sample. Alternatively, the reaction region 40 may have a space for receiving a reaction vessel containing a sample to be able to receive the sample. Examples of the reaction vessel include an individual tube, a strip in the form of multiple tubes connected in row, or a plate resultant from connecting multiple tubes in row and column. Where the reaction region 40 has a space for directly receiving a sample, the space may be referred to as a reaction vessel.

The reaction region 40 may come in various shapes.

An example of the reaction region 40 is a heating block. The heating block may include a plurality of holes, and reaction vessels may be positioned in the holes.

The heating block is formed of a conductive material. The heating block may be heated by a heating element, e.g., a Peltier element or resistor and the heat is transferred to the reaction vessels received in the holes of the heating block. For example, the heating block may be formed of a metal, such as aluminum, gold, silver, nickel, or copper.

Another example of the reaction region 40 is a heating plate. The heating plate may be formed of a plate for receiving samples and a thin metal sheet attached to the plate. The heating plate may be operated in such a manner that the plate is heated by applying electric current to the thin metal sheet.

Another example of the reaction region 40 may be formed of one or more chips or cartirdges. An example of the cartridge is a fluid cartridge including a flow channel.

According to an embodiment, the reaction region 40 comprises n×m wells where n or m is a natural number not less than 2. The reaction region 40 may be shaped as a rectangle in which n x m wells are arranged in a matrix pattern. For example, 4×4 represents 16 wells.

The reaction region may include 2×2, 3×3, 4×4, 5×5, 6×6, 7×7, or 8×8 wells. The reaction region may include 2×4, 3×6, 4×8, 5×10, 6×12, 7×14, or 8×16 wells. The reaction region may include 2×6, 3×9, 4×12, 5×15, 6×18, 7×21, or 8×24 wells. The reaction region may include 2×8, 3×12, 4×16, 5×20, 6×24, 7×28, or 8×32 wells. The reaction region may include 1×8, 8×12, 8×24, 12×16, or 16×24 wells.

The reaction region may include one or more, four or more, 10 or more, 30 or more, 50 or more, or 80 or more wells. The reaction region may include 500 or less, 400 or less, 300 or less, 200 or less, or 100 or less wells.

The reaction region may be divided into two or more light irradiation regions. The light irradiation region denotes a region where simultaneous optic signal detection is possible using light of the same wavelength.

When the reaction region receives a plurality of samples, one light irradiation region includes a×b samples where a or b is a natural number not less than 2. The light irradiation region may be shaped as an a×b rectangle. Or, one light irradiation region incldues two or more reaction vessels.

The device according to the disclosure comprises two or more reaction regions 40.

Each reaction region 40 is thermally independent. In other words, no heat transfer occurs from one reaction region 40 to another reaction region 40. For example, an insulating material or air gap may be present between the reaction regions 40.

The temperature of each reaction region 40 may be independently controlled. For example, while the first reaction region remains at 94° C. at a first time, the second reaction region may be cooled down from 94° C. to 60° C. or heated up from 60° C. to 75° C. or may remain at a specific temperature. Thus, a separate reaction may be performed in each reaction region of the light detection device.

An individual reaction protocol including temperature and time may be set for each reaction region 40. Each reaction region 40 may perform reaction by an independent protocol.

Since reaction is performed in the reaction regions 40 by the independent protocols, the light detection times in the reaction regions 40 are independent from each other.

According to an embodiment, the light detection device 100 may comprise 2, 3, 4, 5, 6, 7, 8, 9, 10, 11, 12, 13, 15, or 16 reaction regions.

According to an embodiment, the light detection device 100 may comprise two or more reaction regions, four or more reaction regions, six or more reaction regions, or eight or more reaction regions. According to an embodiment, the light detection device 100 may comprise 24 or less reaction regions, 20 or less reaction regions, 16 or less reaction regions, or 12 or less reaction regions.

According to an embodiment, the plurality of reaction regions of the light detection device 100 may be configured so that one sample plate may be received over a plurality of reaction regions. Specifically, the reaction regions may have the same array of wells which are places where samples are received in the reaction regions. The reaction regions may be arranged so that the inter-well interval in the reaction regions is the same as the interval between adjacent wells in two adjacent reaction regions.

The optical module 200 comprises two or more light source units 10. The light source unit 10 emits light to excite the optical material (e.g., a dye) contained in the sample. The light emitted from the light source unit 10 may be referred to as an excitation light. The light emitted from the sample may be referred to as an emission light. The path of the excitation light from the light source unit 10 may be referred to as an excitation path. The path of the emission light from the sample may be referred to as an emission path. The light source unit 10 comprises one or more light sources. According to an embodiment, wherein each of the light source units comprises one or more light sources. The terms "light source unit," "light source group," and "light source region" may have the same meaning and be interchangeably used herein. According to an embodiment, the light sources comprised in the same light source unit may emit lights of the same wavelength. Alternatively, one light source unit may comprise light sources that emit lights of different wavelengths. This light source unit is referred to as a multi-wavelength light source unit. Preferably, the multi-wavelength light source unit includes two groups of light sources that generate lights capable of exciting different optical labels. Since the two groups of light sources of the multi-wavelength light source unit each may be independently adjusted, two light of different wavelengths may be selectively radiated from one light source unit. Use of the multi-wavelength light source unit enables detection of two or more optic signals with one light source unit.

According to an embodiment, the light source may be a light emitting diode (LED), including an organic LED, inorganic LED, and quantum dot LED, or a laser unit including a tunable laser, He-Ne laser, or Ar laser. According to an embodiment, the light source may be an LED. Specifically, the light source according to the disclosure may be an LED that produces light of a specific wavelength band.

According to an embodiment, the optical module 200 may comprise two or more light source units that emit different lights. According to an embodiment, the light source units may emit different lights. The different lights are lights of different wavelength bands. The different lights are the lights that is capable of exciting different optical label respectively. According to an embodiment, the light source units may emit lights to excite different optical labels. The optical label may be, e.g., a fluorescent material.

The light source unit 10 irradiates the reaction region 40 with light. The light emitted from the light source unit 10 may excite the fluorescent material present in the sample. The excited fluorescent material may emit fluorescence. The different lights may excite different fluorescent materials present in the sample, and different fluorescent lights.

For example, light of a first wavelength may excite a first fluorescent material, and a light of second wavelength may excite a second fluorescent material. The first and second fluorescent materials may be contained in one reaction vessel.

A plurality of different fluorescent materials may be used for quantitative or qualitative analysis on a plurality of target nucleic acid sequences present in the sample.

The optical module 200 according to the disclosure is configured to be able to receive light source units 10 that emit different lights to be able to excite a plurality of fluorescent materials.

According to an embodiment, the optical module 200 comprises 2, 3, 4, 5, or 6 light source units 10 that emit different lights. According to an embodiment, the optical module 200 comprises two or more, three or more, four or more, or five or more light source units 10 that emit different lights. According to an embodiment, the optical module 200 comprises 10 or less, 8 or less, or 6 or less light source units 10 that emit different lights. According to an embodiment, the light source units comprise four or more light source units capable of radiating four or more different lights.

The light source units 10 in the optical module 200 may be arranged in row or column or radially. The light source units 10 emitting different lights may be arranged symmetrically with respect to a straight line. The light source units 10 emitting different lights may be arranged symmetrically with respect to an axis.

For example, four light source units 10 emitting different lights may be arranged in one row or two rows. Four light source units 10 emitting different lights may be arranged in quadrants with respect to axes.

The optical module 200 is configured to be movable. According to an embodiment, the optical module 200 is configured to be linearly movable forward, backward, to the left or to the right. According to an embodiment, the light source units are linearly arranged. According to an embodiment, as the light source units are simultaneously moved along a straight line, areas irradiated with the light are changed. According to an embodiment, the optical module 200 is configured to rotate around a rotational axis. In particular, the light source units 10 in the optical module 200 are arranged around the rotational axis and are configured to be rotatable around the rotational axis. According to an embodiment, as the light source units are rotated around the rotational axis, areas irradiated with the light by the light source units are changed.

The light source unit 10 irradiates the reaction region 40 with light. The light source unit 10 may be positioned on top of the reaction regions 40. In this case, the light from the light source unit 10 may be emitted directly to the reaction regions. The light source unit 10 may be positioned over the reaction region 40. In this case, the optical path may be adjusted by, e.g., a mirror or beam splitter to allow the light to be radiated to the reaction region. FIG. 1 illustrates an example in which the light source unit 10 is positioned on top of the reaction region 40. Optionally, the light source unit 10 may be placed in the position where the detector 60 is positioned.

As used herein, the phrase "light source unit is positioned at reaction region," "light source unit is positioned for reaction region," or "light source unit is positioned on reaction region" may mean that the light source unit is in the position where the light source unit may irradiate the reaction region 40 with light along the optical path. Thus, the phrase encompasses when the light source unit 10 is positioned over the reaction region, as well as when the light source unit 10 is positioned on top of the reaction region.

The light source unit 10 may radiate light in an area within a predetermined range of the reaction region 40. The area within a predetermined range of the reaction region means an area not more than the area of the reaction region 40. The light source units 10 according to the disclosure are configured to be movable and irradiate the reaction regions with light while moving between the reaction regions. In this case, one light source unit may be configured to irradiate the whole or part of the corresponding reaction region with light. Thus, the light source unit 10 may be configured to radiate light to the whole, or a portion, of the reaction region.

The light source unit 10 may irradiate an area of predetermined size with light. The size of the area of predetermined size may be equal to or less than the size of reaction region. Since the light source units 10 according to the disclosure are configured to be movable, the location where one light source unit 10 irradiates with light may be changed, but the size of the area to which light is irradiated is constant.

In one embodiment, the predetermined size of the area where the light source units 10 of the device irradiates light may be the same.

According to an embodiment, one light source unit 10 may be configured to irradiate the whole or part of one reaction region 40. FIG. 1 illustrates an example in which one light source unit 10 irradiates one whole reaction region 40 with light.

Figure 2:
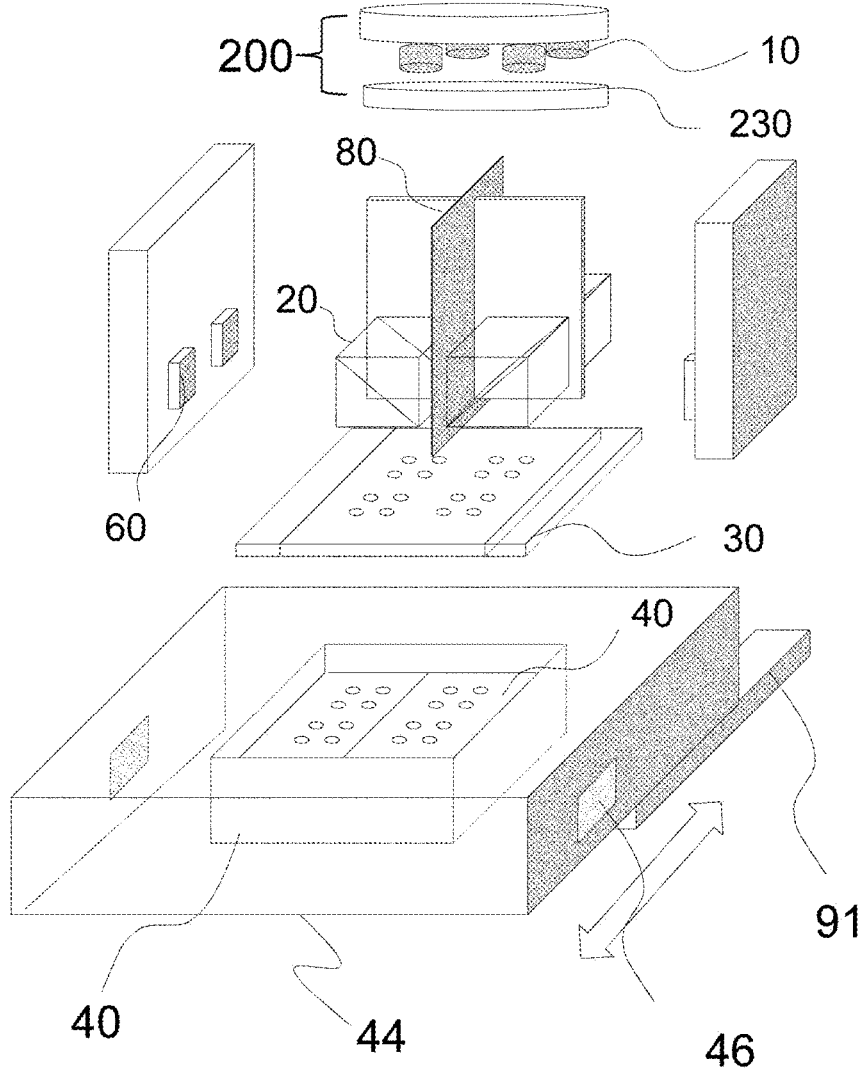
FIG. 2 is a view illustrating a light detection device according to an embodiment of the disclosure.

FIG. 2 illustrates an example in which one light source unit 10 irradiates ½ of one reaction region 40 with light. In this case, the area of predetermined size is ½ of the reaction region 40.

The light irradiation range may be adjusted depending on the area of the reaction region and, if the reaction region includes wells, the number and distribution of the wells, or the distance between the light source unit and the reaction region.

According to an embodiment, the area of a predetermined size may be the area of corresponding to 1/2, 1/3, 1/4, 1/5, or 1/6 of one reaction region in size.

Where the light source unit 10 radiates light to part of the reaction region 40, two or more light source units 10 may separately radiate the light to one entire reaction region by deviding the one entire reaction region.

FIG. 2 illustrates an example in which two light source units 10 respectively radiate light to the halves of the reaction region 40.

According to an embodiment, the optical module 200 is configured so that two, three, or four light source units separately irradiate one reaction region 40 with light.

Figure 5:
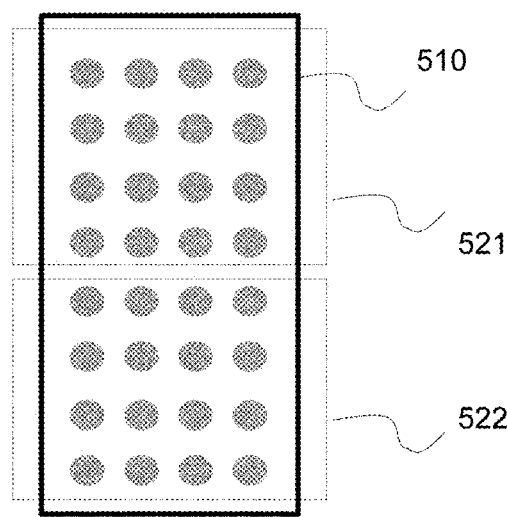
FIGS. 5 and 6 are views illustrating the relationship between a reaction region and a light irradiation region, wherein the solid lines denote the reaction region, the dashed lines denote the light irradiation region, and the dots denote the wells for receiving samples.
Figure 6:
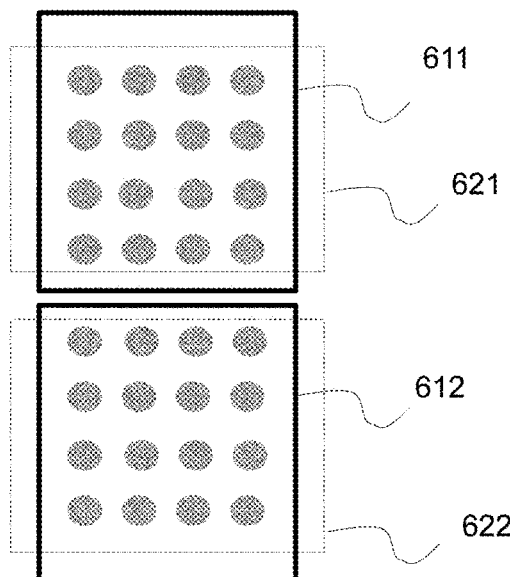

FIGS. 5 and 6 are views illustrating the relationship between the reaction region and the light irradiation region. The solid lines denote the reaction region, and the dashed lines denote the light irradiation region. The light irradiation region may denote a unit of range in which one light source unit radiates light or a unit of light irradiation by one light source unit in the reaction region.

FIG. 5 illustrates an example in which one heating block 510 with a plurality of wells are irradiated with light by two light source units 10. The area irradiated with different lights may be divided into light irradiation regions 521 and 522. Due to one reaction region 40, the two light irradiation regions 521 and 522 have the same temperature. Thus, the two light irradiation regions 521 and 522 may simultaneously reach the detection time. When the two light irradiation regions 521 and 522 reach the detection time, the light source units 10 radiate light to the two light irradiation regions 521 and 522. Despite one reaction region 40, light of different wavelengths may be radiated to the two light irradiation regions.

FIG. 6 illustrates an example in which one heating block 611 or 612 is irradiated with light by one light source unit 10. One heating block has one light irradiation region 621 or 622. Since the temperatures of the two heating blocks 611 and 612 are independently controlled, the temperatures of the two light irradiation regions 621 and 622 may be identical to or different from each other. Thus, the two light irradiation regions 621 and 622 may have the same or different detection times. When any one of the two light irradiation regions 621 and 622 reaches the detection time, light is radiated to the light irradiation region which has reached the detection time. When the two light irradiation regions 621 and 622 both reach the detection time, the two light irradiation regions 621 and 622 both are irradiated with light. The two light irradiation regions 621 and 622 may be irradiated with light of different wavelengths.

According to an embodiment, the reaction region 40 includes a plurality of wells. The wells may receive samples or sample-containing reaction vessels. The light irradiation region irradiated with light by one light source unit includes a plurality of wells. For example, a plurality of, e.g., 10 or more, 16 or more, 20 or more, 32 or more, or 40 or more, wells may be simultaneously irradiated with light.

According to an embodiment, the area where the light source units radiate light while moving over the reaction region 40 is fixed. For example, the areas irradiated with light by the light source units, of the reaction region in FIG. 5 are a first light irradiation region 521 and a second light irradiation region 522. Where a new light source unit is moved to the position where it may irradiate the reaction region as the optical module moves, the light source unit irradiates the first light irradiation region 521 or the second light irradiation region 522 with light, and the number of wells irradiated with the light or the area irradiated with light is not newly set.

According to the disclosure, a movable optical module 200 is used to enable light detection, in a more efficient manner, on the plurality of reaction regions 40 where reaction is perofrmed by independent protocols. The movement of the optical module 200 repositions the light source unit included in the optical module 200, thus enabling light detection on a plurality of reaction regions 40.

By light detection according to the disclosure, e.g., when a target analyte is present in the sample, the optical module 200 radiates an excitation light suitable for the optical label to the sample to be able to generate an optic signal indicating the presence of the target analysis material, and the detector senses the emission light from the sample. Detection of light from two reaction regions means performing radiation of excitation light and sensing of emission light on the samples received in the reaction regions, in both the two reaction regions. Performing light detection only on the first reaction region but not on the second reaction region means that any one of radiation of excitation light by the optical module and sensing of emission light by the detector is not performed on the second reaction region or neither radiation of excitation light by the optical module nor sensing of emission light by the detector is performed on the second reaction region.

According to an embodiment, the light source units may be simultaneously moved, and areas irradiated with the light by the light source units may be simultaneously changed.

FIG. 1 illustrates an example in which two light source units 10 respectively radiate light to two reaction regions 40. The two light source units 10 are arranged around the rotational axis in the optical module 200 and, as the optical module 200 rotates, the areas irradiated with light by the light source units 10 may simultaneously be changed. Changing the area irradiated with light by the light source unit means that as the light source unit moves, a different place from the prior one is irradiated with the light.

For example, the first light source unit irradiates the left-hand first reaction region with light, and the second light source unit irradiates the right-hand second reaction region with light. Thereafter, as the optical module 200 rotates, the first light source unit moves to be able to irradiate the second reaction region with light while the second light source unit simultaneously moves to irradiate the first reaction region with light.

The light source units are positioned on the light irradiation region on the reaction region which reaches the light detection time of the reaction regions and radiate light.

According to an embodiment, in the device according to the disclosure, each light source unit may radiate light, at least once, to the reaction region which reaches the light detection time of the reaction regions.

For example, when the left-hand first reaction region reaches the light detection time, one light source unit radiates light to the first reaction region and, as the optical module 200 rotates (i.e., the light source units 10 are rotated at 180 degrees), different light source units sequentially radiate light to the first reaction region.

While the light source units 10 are sequentially positioned on the first reaction region, other light source units 10 may sequentially be positioned on the right-hand second reaction region. Unless the second reaction region reaches the light detection time, the light source units 10 positioned on the second reaction region may be controlled not to radiate light.

Meanwhile, if the second reaction region also reaches the light detection time, the light source units 10 positioned on the second reaction region may be controlled to radiate light. Where one reaction region is configured to be separately irradiated with light by a plurality of light source units, each light source unit may be configured to radiate light, two or more times, to the reaction region reaching the light detection time. According to an embodiment, the reaction regions comprise a first reaction region and a second reaction region, wherein the light source units comprise a first light source unit and a second light source unit, and wherein when the first reaction region and the second reaction region simultaneously reach a light detection time, as the light source units are rotated, the first light source unit is positioned in the first reaction region, and the second light source unit is positioned in the second reaction region to synchronously irradiate different areas with different lights.

According to an embodiment, the optical module 200 may radiate light to the reaction regions 40 while linearly moving. The optical module 200 may be configured to move to the left and right, forward and backward, or in a combination thereof.

For example, if the left-hand first reaction region reaches the light detection time, the left-hand first light source unit radiates light. As the optical module 200 moves to the left, the right-hand second light source unit is positioned on the first reaction region and radiates light. The optical module 200 may be in the position when the light irradiation is terminated or may be moved to its initial position. The initial position may be the center or any one side.

If the right-hand second reaction region also reaches the light detection time, the second reaction region may be irradiated with light by the light source unit which is positioned on the second reaction region at the time.

Where the optical module 200 linearly moves in the above example, such an occasion may arise where a light source unit is positioned on some reaction region, but no light source unit is positioned on other reaction regions.

FIG. 2 is a view illustrating a light detection 100 device according to an embodiment of the disclosure. Referring to FIG. 2, a light detection device 100 comprises an optical module including four light source units 10 and two reaction regions 40.

According to an embodiment, the light source units may be rotated around the rotational axis at 90 degrees, 180 degrees, 270 degrees, or 360 degrees. According to an embodiment, the light source units are rotated around the rotational axis in 90-degree increments.

Among the four light source units 10, two light source units 10 are positioned on one reaction region, and the other two light source units 10 are positioned on the other reaction region. Thus, one reaction region 40 includes two light irradiation regions.

The four light source units 10 may be simultaneously repositioned by rotation. In the instant embodiment, the light source units 10 may change their position as they rotate by 90 degrees.

For example, the left-hand reaction region is denoted a first reaction region, and the right-hand reaction region is denoted a second reaction region. The lower half and upper half of the first reaction region are denoted a first light irradiation region and a fourth light irradiation region, respectively, and the lower half and upper half of the second reaction region are denoted a second light irradiation region and a third light irradiation region, respectively.

At a predetermined time, the light source unit in the position where it radiates light to the first light irradiation region is denoted a first light source unit, the light source unit in the position where it radiates light to the second light irradiation region is denoted a second light source unit, the light source unit in the position where it radiates light to the third light irradiation region is denoted a third light source unit, and the light source unit in the position where it radiates light to the fourth light irradiation region is denoted a fourth light source unit. In the above example, the second light source unit, the third light source unit, and the fourth light source unit are arranged one-by-one clockwise from the first light source unit.

As the optical module 200 rotates clockwise, the first to fourth light source units may sequentially be positioned on the first light irradiation region of the first reaction region. Where the first reaction region reaches the detection time, the first light source radiates light to the first light irradiation region of the first reaction region. The light source units are rotated at 90 degrees, and the second light source radiates light to the first light irradiation region of the first reaction region. The light source units are rotated at 90 degrees, and the third light source radiates light to the first light irradiation region of the first reaction region. The light source units are rotated at 90 degrees, and the fourth light source radiates light to the first light irradiation region of the first reaction region.

As the optical module 200 rotates, the first light source unit which used to be positioned on the first light irradiation region of the first reaction region may be repositioned on the fourth light irradiation region of the first reaction region. Thus, the fourth light irradiation region of the first reaction region which has reached the detection time may be irradiated with the same light as the light radiated to the first light irradiation region of the first reaction region.

Meanwhile, in a case where the first light source unit is positioned on the first light irradiation region of the first reaction region, since the fourth light source unit is also positioned on the fourth light irradiation region of the first reaction region, the fourth light irradiation region of the first reaction region may be irradiated with light, starting from light irradiation by the fourth light source unit, sequentially by the first light source unit, the second light source unit, and the third light source unit.

Further, where the first light source unit and the fourth light source unit are positioned on the first reaction region, the second light source unit and the third light source unit may also be positioned on the second reaction region. Where the second reaction region also reaches the detection time, the second reaction region may be irradiated with light first by the second light source unit and the third light source unit. Thereafter, as the light source units are sequentially rotated, the remaining light source units may radiate light to the second reaction region.

According to an embodiment, the optical module 200 may linearly move. The four light source units may be arranged in a matrix pattern or in a row. According to an embodiment, one light source unit may be configured to irradiate the entire reaction region with light.

The optical module 200 may be configured to move to the left and right, forward and backward, or in a combination thereof.

According to the disclosure, the light source unit 10 may be moved to allow the reaction region to be irradiated with necessary light.

According to the disclosure, when one light source unit is positioned on one reaction region, the optical module 200 may allow another light source unit to be positioned on another reaction region, and light detection may be synchronously performed on the two reaction regions 40 using different lights. According to an embodiment, at least one of the light source units is positioned in one reaction region, and at least one other light source unit is positioned in another reaction region so that different reaction regions may be synchronously irradiated with different lights.

The synchronous light detection may encompass the case where optic signals for two reaction regions are measured at the same time. The synchronous light detection may also encompass the case where although the times of measurement of optic signals for, e.g., two reaction regions do not simply overlap each other, the optic signal for one reaction region is measured and, then, the optic signal for the other reaction region is measured without any physical component, e.g., a light source or filter for the device. The synchronous measurement may also encompass the case where measurement data of the optic signals for, e.g., two reaction regions is treated as obtained in substantially the same time period.

As the optical module 200 rotates or linearly moves, the light irradiation regions of the light source units are simultaneously changed.

According to an embodiment, use of the optical module which is rotated to move the light source units allows all of the light source units in the optical module to always have the light irradiation region on the reaction region upon rotating the optical module 200 to reposition the light source units. FIG. 2 illustrates an example of such a configuration of the optical module 200 and the reaction regions 40.

As used herein, the phrase "reaction region 40 reaches detection time" may mean that the reaction region has reached the detection temperature or that the time of irradiating the reaction region 40 with light has arrived.

As used herein, the phrase "light source units 10 are located on reaction region 40" means that the light source units 10 are moved to the position where they may irradiate the light irradiation region with light.

According to an embodiment, if one reaction region reaches the detection time, the light source units may sequentially be positioned on one reaction region to radiate light to the reaction region and, if another reaction region reaches the detection time, the light source units sequentially positioned on the other reaction region radiate light to the other reaction region.

According to an embodiment, if one reaction region reaches the light detection time while another reaction region simultaneously reaches the detection time or if, while one reaction region, which has reached the light detection time, is irradiated with light, another reaction region reaches the detection time, the light source unit positioned on the other reaction region may radiate light to the other reaction region. In this case, the lights radiated to the different reaction regions may be different lights.

Where light source units 10 of different wavelengths may be positioned on different regions in the reaction region 40, if the reaction region 40 reaches the detection time, the light source units 10 of different wavelengths may radiate light to the light irradiation regions synchronously assigned.

According to an embodiment, the light detection device 100 may be configured so that each of the light source units 10 included in the optical module 200 is positioned on any one reaction region of the reaction regions 40. In other words, the light detection device 100 may be configured so that none of the light source units 10 are not positioned on the reaction region. In particular, the light detection device 100 is configured so that even when the optical module 200 moves (in particular, when it rotates), each light source unit is positioned on any one reaction region. According to an embodiment, the light detection device 100 is configured so that each light source unit included in the optical module 200 is able to have a light irradiation region in any one reaction region among the reaction regions.

According to an embodiment, the light detection device 100 is configured so that the optical module 200 comprising two to six light source units 10 for providing light of different wavelengths and configured to allow one or two light source units 10 to irradiate one reaction region 40 with light is able to radiate light to two to six reaction regions 40.

The beam splitter 20 may reflect or transmit the light incident from the light source unit 10. According to an embodiment, the light transmitted through the beam splitter 20 passes through the hole of the pressure lid 30 to the reaction region 40. The beam splitter 20 may reflect and transmit the light emitted from the sample. According to an embodiment, the light reflected by the beam splitter 20 arrives at the detector 60. The light emitted from the sample may be referred to as light or an optic signal.

According to an embodiment, the light reflected by the beam splitter 20 passes through the hole of the pressure lid 30 to the reaction region 40. According to an embodiment, the light transmitted through the beam splitter 20 arrives at the detector 60.

The pressure lid 30 provides pressure to the reaction vessels of the reaction region 40. The pressure lid 30 may contact the covers of the reaction vessels and press the covers of the reaction vessels, providing pressure to the reaction vessels. The pressure lid 30 may maintain a high temperature. For example, the pressure lid 30 may include a heat plate (not shown) to maintain a temperature of 105° C.

The pressure lid 30 comprises a plurality of holes. The holes of the pressure lid 30 are formed in the positions corresponding to the reaction vessels 40 containing samples in the reaction region so that an optical path may be formed between the sample and the light source.

A light-blocking wall 80 is used to prevent interference between the lights emitted from the light source units 10. The light-blocking wall 80 is used to prevent interference between the fluorescent lights emitted from the samples.

The light-blocking wall 80 is installed considering the path of the excitation light radiated from the light source unit 10 and the emission light emitted from the sample.

The light-blocking wall 80 may be disposed between adjacent light source units. The light-blocking wall 80 may be disposed between adjacent detectors.

According to an embodiment, the light-blocking wall 80 may be shaped as a rectangular or circular tube. According to an embodiment, the light-blocking wall 80 may be shaped as a combination of a plurality of tubes. According to an embodiment, a beam splitter may be positioned inside the light-blocking wall 80.

A reaction region housing 50 may receive the reaction region 40 and the element (e.g., a heat transfer element (not shown) or a heat radiating plate (not shown)) used to heat or cool the reaction region. The heat transfer element increases or decreases the temperature of the heating block. The heat transfer element may be positioned under the heating block in contact with the heating block to transfer heat to the heating block. As an example, the heat transfer element may be a Peltier element. The heat radiating plate is positioned under the heat transfer element to radiate the heat generated from the heat transfer element.

The detector 60 detects signals. Specifically, the detector 60 detects the emission lights generated from the samples. The detector may sense the amount of light per wavelength distinctively or may sense the total amount of light regardless of wavelengths. Specifically, the detector may use, e.g., a photodiode, a photodiode array, a photo multiplier tube (PMT), a charge-coupled device (CCD) image sensor, a complementary metal-oxide-semiconductor (CMOS) image sensor, or an avalanche photodiode (APD).

According to an embodiment, one or more different detectors may be assigned to each reaction region, and the light emitted from each reaction region may be measured by one or more different detectors assigned. According to an embodiment, one or more detectors may be disposed for one reaction region.

According to an embodiment, where one light source unit 10 is configured to irradiate one entire reaction region with light, one detector is used per reaction region.

Figure 7:
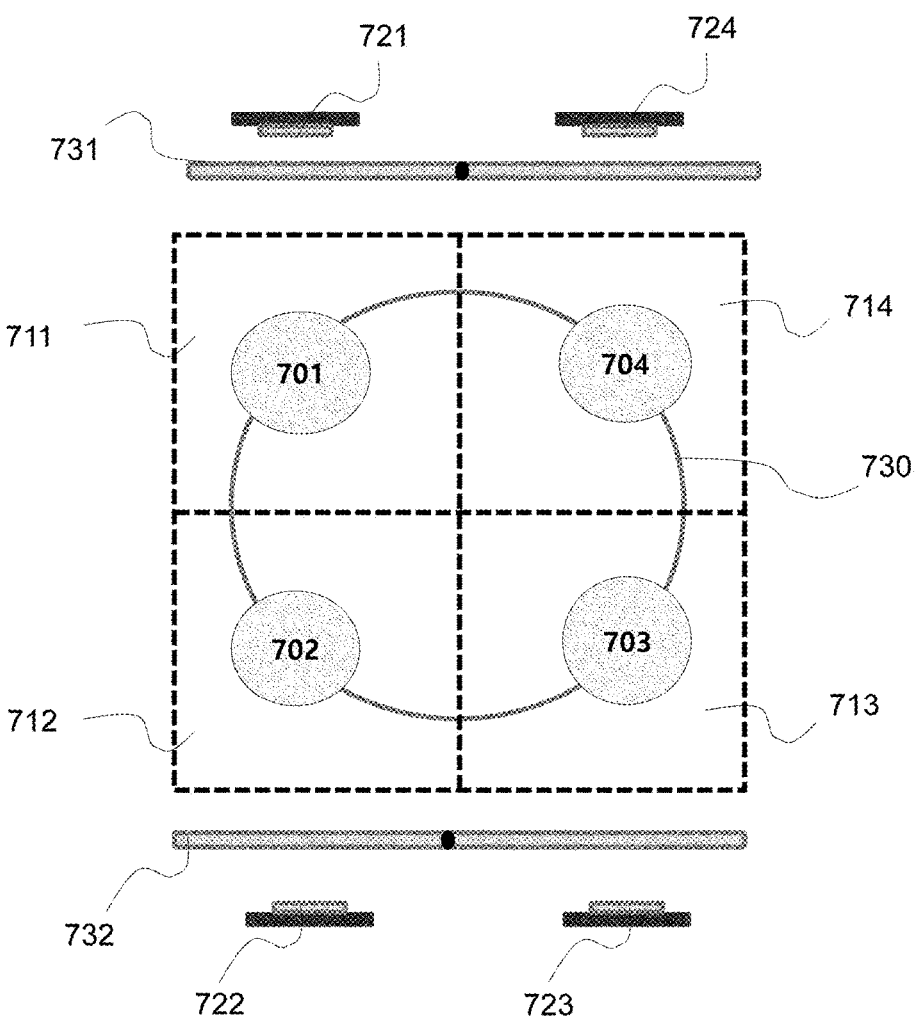
FIG. 7 is a view illustrating a light irradiation process by rotation of a light source wheel.

According to an embodiment, where a plurality of light source units 10 are configured to separately irradiate sections divided into from one reaction region with light, as many detectors as the number of the light source units used for irradiating the one reaction region with light are used. According to an embodiment, one detector is disposed for an area irradiated with the light by one light source unit in one reaction region. A detector is disposed for the area assigned to each light source unit. According to an embodiment, one or more different detectors of the detectors are assigned to each of the reaction regions, and light emitted from each reaction region is measured by the one or more different detectors assigned. According to an embodiment, two or more different detectors among the detectors may be assigned to each reaction region, and the light emitted from each reaction region may be measured by the two or more different detectors assigned. Specifically, two or more detectors may be assigned for one reaction region to detect emission lights. In this case, each detection zone for the two or more detectors may be allocated on one reaction region, and the two or more detectors may separately sense the emission lights for sections divided into from one reaction region. FIG. 7 is a view illustrating an example of light irradiation and sensing of emission light for the reaction region. Although no reaction region is shown, the first reaction region includes a light irradiation region 711 and a light irradiation region 714. The second reaction region includes a light irradiation region 712 and a light irradiation region 713. Referring to FIG. 7, since each reaction region is shaped as a rectangle, if the emission lights from all the samples in one reaction region are sensed using one detector, the distance between the reaction region and the detector may increase. As two detectors 721 and 724 are configured to detect emission lights from one reaction region 711 and 714 sectioned, the reaction region and the detector may remain sufficiently close to each other. Thus, it is possible to sense optic signals of a smaller amount of light, and inter-well signal deviation may be mitigated. According to an embodiment of the disclosure, the regions where the detectors sense light may be distinct areas which do not overlap each other. In other words, the emission lights from all the samples received in the device according to the disclosure may be sensed by only one detector of the plurality of detectors.

The optical module may further comprise an optical filter.

According to an embodiment, the optical filter is used to filter the light emitted from the light source unit.

In the case of an optical module using rotational light source units, when the light source units are rotated, the filter of the corresponding light source unit may be rotated together.

According to an embodiment, the optical module comprises an optical filter wheel.

Referring to FIG. 2, the optical module includes the optical filter wheel 230.

The optical filter wheel 230 includes one or more optical filters. The optical filters 250 filter the light emitted from the light source units 10. The optical filter 250 transmits the light emitted from the light source 10. For example, the optical filter 250 may be a bandpass filter.

Although FIG. 2 illustrates four beam splitters 20, the beam splitters 20 in the same direction for the detectors positioned on the same surface may be replaced with a single beam splitter 20. Thus, two beam splitters 20 may be disposed for four light source units.

One pressure lid 30 may cover a plurality of reaction regions. Referring to FIG. 2, one pressure lid 30 may apply pressure to two reaction regions.

Referring to FIG. 2, the light detection device 100 includes four detectors 60.

The number of detectors 60 may be identical to the number of light irradiation regions into which the reaction region is divided. That is, each of the detectors 60 may correspond to a respective one of the light irradiation regions.

Figure 3:
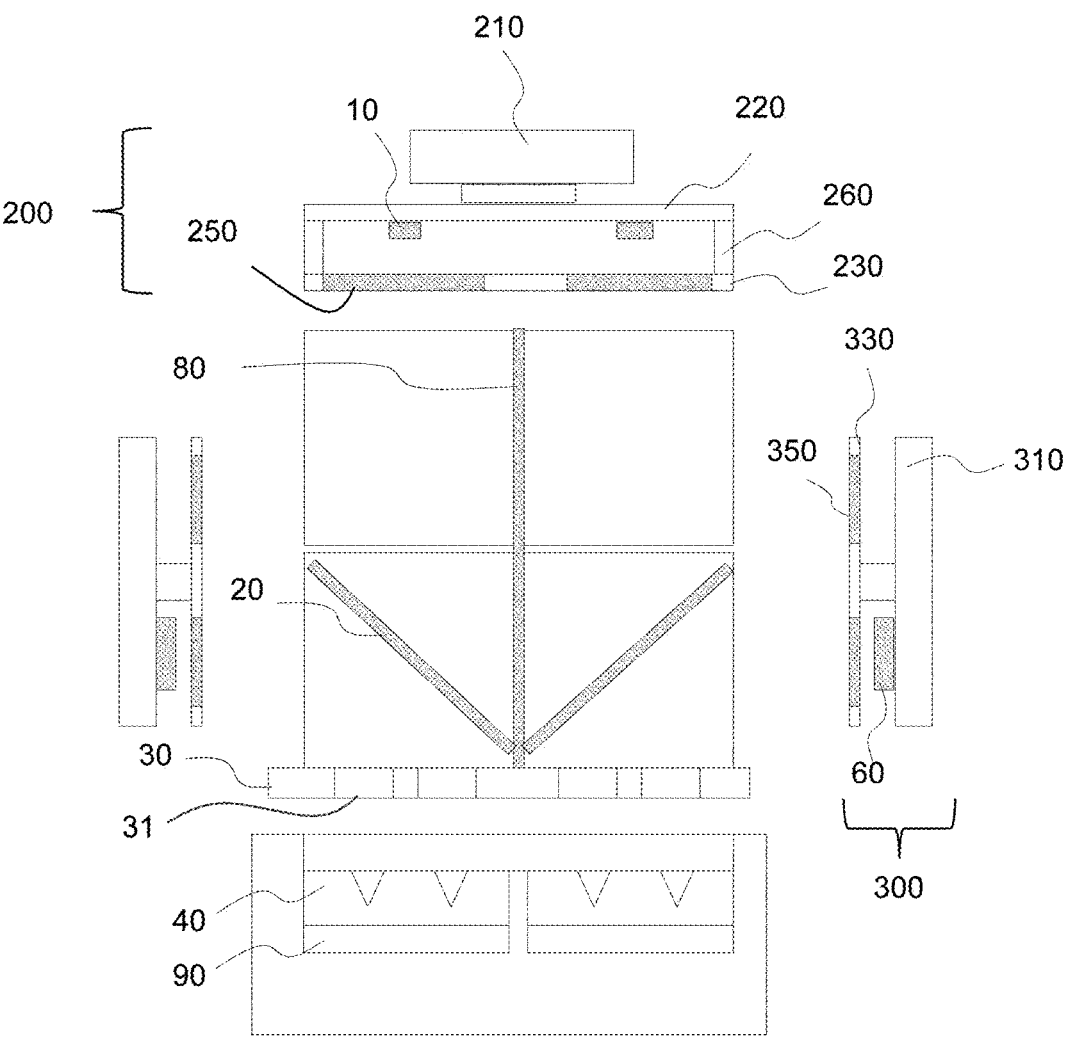
FIG. 3 is a front view illustrating a light detection device according to an embodiment of the disclosure.

FIG. 3 is a front view illustrating a light detection device 100 according to an embodiment of the disclosure.

Optical filters 250 may be positioned on the optical paths of the light source units 10. The optical filters 250 may be rotated along with the light source units 10. As the light source wheel 220 is coupled with the optical filter wheel 230, they may be rotated by one motor 210.

The light source wheel 220 and the optical filter wheel 230 may be structured to be independently separated from each other. The light source wheel 220 may be separated from the optical filter wheel 230, with the light source units 10 fixed to the light source wheel 220. The optical filter wheel 230 may be separated from the light source wheel 220, with the optical filters 250 fixed to the optical filter wheel 230.

Such a structure allows for convenient management of the light source wheel 220 and the optical filter wheel 230 and easier assembly of the optical module.

At least two or more light source units 10 among the light source units in the light source wheel 220 may emit lights of different wavelengths. As an example, where the light source wheel 220 includes two light source units, each light source unit 10 may emit light of a different wavelength. As an example, where the light source wheel 220 includes three light source units, the three light source units 10 may emit lights of different wavelengths respectively, or two light source units 10 may emit light of the same wavelength while the other light source unit 10 may emit light of different wavelengths.

According to an embodiment, the light source wheel 220 may comprise four light source units, and each of the light source units 10 may emit lights of a different wavelength respectively.

The positions of the light source units are simultaneously changed by the rotation of the light source wheel 220. In other words, the positions of the light source units are rotated as the light source wheel 220 spins. For example, where the light source wheel 220 includes two light source units, the first light source unit and the second light source unit may switch their positions. Where the light source wheel 220 includes three light source units, as the motor 210 rotates, the first light source unit moves to the position of the second light source unit, the second light source unit moves to the position of the third light source unit, and the third light source unit moves to the position of the first light source unit. Where the light source wheel 220 includes four light source units, as the motor 210 rotates, the first light source unit moves to the position of the second light source unit, the second light source unit moves to the position of the third light source unit, the third light source unit moves to the position of the fourth light source unit, and the fourth light source unit moves to the position of the first light source unit.

In the disclosure, such repositioning may be referred to as "cyclic movement."

According to an embodiment, the light source wheel 220 comprises the first light source unit and the second light source unit, and two or more first LEDs are disposed in the first light source unit to emit light of the first wavelength. Two or more second LEDs are disposed in the second light source unit to emit light of the second wavelength.

The light source wheel 220 and the optical filter wheel 230 are rotated at 360/n degrees at a time by the motor 210. Here, n is a natural number not less than two. According to an embodiment, when the light source wheel 220 includes two light source units 10, and the optical filter wheel 230 includes two filters 250, the light source wheel 220 and the optical filter wheel 230 are rotated at 180 degrees at a time by the motor 210.

As another example, when the light source wheel 220 includes three light source units 10, and the optical filter wheel 230 includes three filters 250, the light source wheel 220 and the optical filter wheel 230 are rotated at 120 degrees at a time by the motor 210.

As still another example, when the light source wheel 220 includes four light source units 10, and the optical filter wheel 230 includes four filters 250, the light source wheel 220 and the optical filter wheel 230 are rotated at 90 degrees at a time by the motor 210.

The light source wheel 220 and the optical filter wheel 230 may have light source units and filters which mutually correspond to each other and are assembled so that the light source units and the filters corresponding to each other may be aligned. The filters 250 are aligned to be positioned on the paths of the lights emitted from the light source units. Specifically, the filter 250 is positioned on the path of the light emitted from the light source received in the light source unit 10. The light source wheel 220 and the optical filter wheel 230 are rotated, with the light source units and the filters remaining aligned. Where the light source wheel 220 and the optical filter wheel 230 are fixed by a connection structure 260, the light source wheel 220 and the optical filter wheel 230 remain aligned despite rotation.

As an example, the connection structure 260 may connect the light source unit 10 and the filter 250. When the optical module 200 includes four light source units and four filters, the optical module 200 may include four connection structures. The connection structures 260 may be cylinders connecting the edges of the light source wheel 220 and the optical filter wheel 230. The light emitted from the light source unit 10 may reach the optical filter 250 through the inside of the connection structure 260.

The light-blocking wall 80 is disposed between the optical module 200 and the beam splitter 20, and the pressure lid 30 is disposed under the beam splitter 20. The pressure lid 30 comprises a plurality of holes 31. The light emitted from the light source 10 reaches the heating block through the holes 31.

A detection filter wheel 330 including two or more detection filters 350 may be disposed in front of the detector 60. The detection filter wheel 330 may be positioned ahead of the detector 60 and be rotated as the light source wheel 220 rotates.

The detection filter 350 may be disposed in front of the detector 60. The detection filter 350 disposed in front of the detector 60 may be changed depending on the wavelength of the light emitted from the light irradiation region. For example, where the first light source unit 10 emits a light of the first wavelength to the first reaction region, a first detection filter may be disposed before a first detector 60. Where the second light source unit 10 emits a light of the second wavelength to the first reaction region, a second detection filter may be disposed before the first detector 60.

A plurality of optical filters 250 are disposed in the optical filter wheel 230.

A plurality of detection filters 350 are disposed in the detection filter wheel 330.

The detector 60 generates an electrical signal depending on the strength of the light and detects the light.

According to an embodiment, the detector 60 is disposed in a fixed position.

According to an embodiment, although the optical module 200 rotates, the detector 60 does not rotate. The detector 60 may be disposed in a distance for covering the light emitted from the reaction region 40.

There may be provided one or more detectors 60. A filter may be disposed before the detector 60 to filter the light incident to the detector 60. The filter disposed before the detector 60 may be changed depending on the wavelength.

The detection module refers to an element comprising the detector and the detection filter wheel.

The device according to the disclosure comprises a controller. The controller (not shown) may be, e.g., a computer, a micro-processor, or a programmable logic device. There may be provided one or more controllers. The controller may be electrically connected with a device for controlling the temperature of the reaction regions, a power supply device for the light sources or detectors, and a motor for moving the light source wheel, optical filter wheel, or the detection filter wheel.

The controller independently controls the temperature of the reaction regions 40 and controls the movement of the optical module to allow the light source units 10 to be positioned on the reaction region 40, which has reached the detection time, among the reaction regions 40.

The controller controls the temperature of the reaction regions independently. Independently controlling the temperature means that the controller may separately control the temperature of each reaction region. According to an embodiment of the disclosure, the controller may receive a reaction protocol for each reaction region and may independently control the temperature of the reaction regions according to the received protocols.

The protocol or reaction protocol means a set of instructions to perform a unit operation. The unit operation may include the operation of controlling temperature over time and the operation of measuring signal. The protocol may include information regarding the order and timings of performing various unit operations in the protocol. Specifically, the protocol may be a series of instructions for the order and timings of a series of operations, such as temperature adjustment, excitation light irradiation, and emission light detection which are performed on the sample to perform light detection on the sample. The controller receives the protocol and operates the light detection device so that the operations or effects according to the protocol may be applied to the sample. According to an embodiment, the controller may independently control on/off of light irradiation of the light source units. The controller may independently control the on/off the light source units according to the reaction protocols of the reaction regions to control the light source units to synchronously or asynchronously emit light. The on/off of each light source unit may be independently controlled so that only some light source units emit light or all of the light source units emit light. The controller may control the power supply device to supply power to the light source units corresponding to the reaction region which has reached the detection time.

Further, the controller controls the movement of the light source units. The control may be to control the motor for moving the light source wheel receiving the light source units. The controller controls to allow a proper light source unit to be positioned on the reaction region according to the reaction protocol. Specifically, the controller may control to allow the first light source unit to be positioned on the first reaction region and the second light source unit to be positioned on the second reaction region at a first time and may control to allow the second light source unit to be positioned on the first reaction region and the third light source unit to be positioned on the second reaction region at a second time. The phrase "first light source unit is positioned on the first reaction region" means that the first light source unit is positioned to be able to radiate light to the first reaction region. The controller may control the on/off of the detector for detecting the light emitted from the light irradiated region and the driving of the detection filter wheel.

The controller may control the motor that moves the detection filter wheel receiving the detection filters to position the detection filter corresponding to the emission light generated from the reaction region according to the reaction protocol. Further, the controller may independently control the on/off of the detectors according to the reaction protocol and thus control the detectors to detect the lights synchronously or asynchronously emitted from the reaction region.

As such, the controller may receive the protocol for each sample and operate each component of the light detection device 100 so that temperature control and optic signal measurement are performed in an order defined in the reaction protocol.

The controller may control the movement and heating of the pressure lid 30 and may comprehensively control the driving of the optical module, reaction regions, and detection module.

Figure 4:
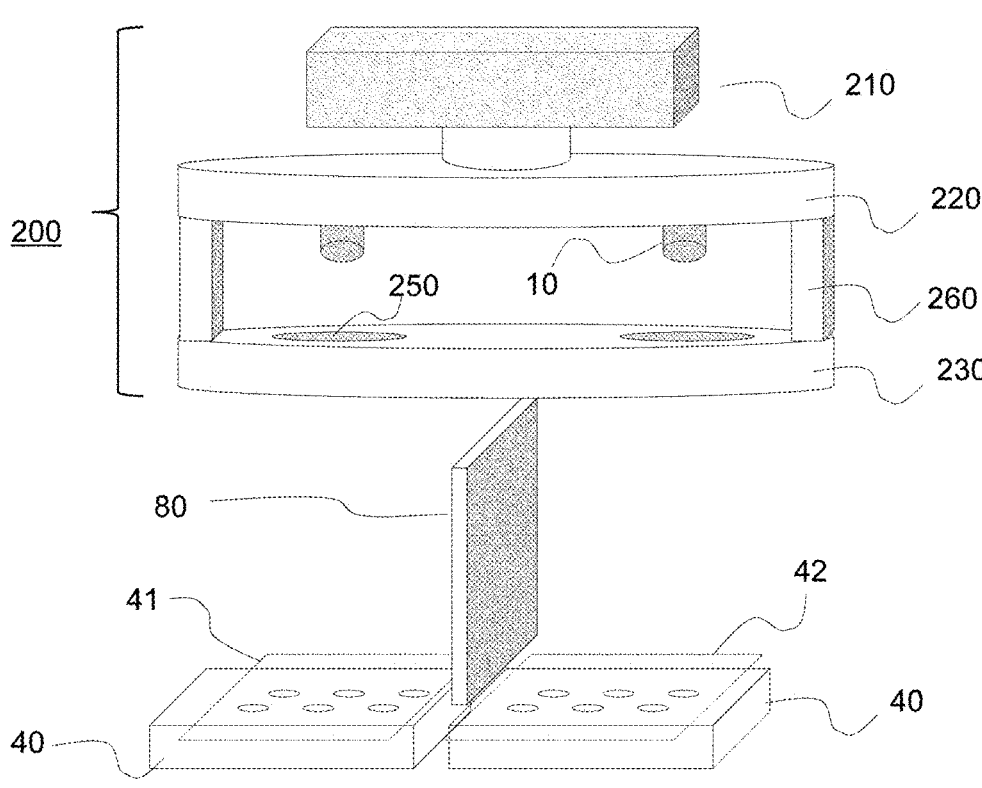
FIG. 4 is a view illustrating an optical module according to an embodiment of the disclosure.

FIG. 4 is a view illustrating a method of light irradiation using the optical module 200. Described is an example in which the optical module 200 may radiate light to the light irradiation region 41 on the reaction region 40, and the detector 60 detects the light emitted from the light irradiation region 41. For ease of description, the beam splitter 20 is omitted, and the optical module 200 is briefly shown with two light source units 10.

The light source wheel 220 and the optical filter wheel 230 are rotated by the motor 210, and the light source units 10 radiate light to the light irradiation region 41. Light is emitted from the light irradiation region 41 and is reflected by the beam splitter 20 to the detector 60. The direction in which the optical module 200 rotates is perpendicular to the direction of the light emitted from the optical module 200.

According to an embodiment, the optical module 200 may be disposed on the reaction regions. In particular, the light source wheel 220 and optical filter wheel 230 of the optical module 200 may be disposed in parallel with the reaction regions. The light emitted from the optical module 200 may be vertically incident to the reaction regions.

FIG. 4 is a view illustrating an optical module 200 according to an embodiment of the disclosure. The optical module 200 includes a motor 210, a light source wheel 220, and an optical filter wheel 230.

The optical module 200 may further include a connection structure 260. The connection structure 260 connects the light source wheel 220 and the optical filter wheel 230. The connection structure 260 connects the respective edges of the light source wheel 220 and the optical filter wheel 230. Although in the example shown, the connection structure 260 is shaped as a rectangular column, the connection structure 260 may be configured in other various shapes, e.g., a plate or cylinder. As an example, the connection structure 260 may be shaped to surround the light source wheel 220 and the optical filter wheel 230.

The light source units 10 emit light for exciting samples. The light source units 10 emit light of the same or different wavelengths. The wavelength includes not only a specific wavelength but also a wavelength band. For example, the wavelength may be 400 nm or may be a wavelength band ranging from 390 nm to 410 nm.

The light source wheel 220 receives a plurality of light source units 10. The light source wheel 220 receives two or more light source units 10. The light source wheel 220 receives the light source units 10 may mean that the light source units 10 are attached to the light source wheel 220. The light source wheel 220 receives the light source units 10 may mean that the light source units 10 may be fixed to a specific position of the light source wheel 220. The light source units 10 may be attached to one end surface of the light source wheel 220. As an example, the light source units 10 may be attached to the bottom end surface of the light source wheel 220. The bottom end surface of the light source wheel 220 means the end surface facing the optical filter wheel 230. The top end surface of the light source wheel 220 means the end surface facing the motor 210.

Although it is shown that the light source wheel 220 receives two light source units 10, the light source wheel 220 may receive three or more light source units 10.

The light source wheel 220 may be rotated by the motor 210 and may be shaped as a circle, ellipse, rectangle, or square.

The positions of the light source units 10 may simultaneously be changed by the rotation of the light source wheel 220.

The optical filter wheel 230 receives a plurality of optical filters 250. The light filter wheel 230 receives the light filters 250 may mean that the light filters 250 are included in the optical filter wheel 230. The light filter wheel 230 receives the light filters 250 may mean that the light filters 250 are fixed to a specific position of the optical filter wheel 230.

The optical filter wheel 230 may be rotated and be shaped as, e.g., a circle, ellipse, rectangle, or square. Although the optical filter 250 is shown as circular, the optical filter 250 may be shaped as a circle, ellipse, rectangle, or square.

The positions of the optical filters 250 may simultaneously be changed by the rotation of the optical filter wheel 230. For example, where the optical filter wheel 230 includes four optical filters 250, as the optical filter wheel 230 rotates, the first optical filter may move to the position of the second optical filter, the second optical filter may move to the position of the third optical filter, the third optical filter may move to the position of the fourth optical filter, and the fourth optical filter may move to the position of the first optical filter.

The optical filters 250 filter the light emitted from the light source units 10. The optical filter 250 filters light may mean that part of the light incident to the optical filter 250 is transmitted while the rest is blocked. For example, where the optical filter 250 is a bandpass filter, the optical filter 250 transmits the light of a wavelength included in the band and blocks the light of a wavelength not included in the band.

The light source wheel 220 and the optical filter wheel 230 may be disposed in parallel with each other. Thus, the direction in which the motor 210 rotates is identical to the direction in which the light source wheel 220 and the optical filter wheel 230 rotate.

Since the light source wheel 220 and the optical filter wheel 230 are fixed together by the connection structure 260, the light source wheel 220 and the optical filter wheel 230 are rotated together as the motor 210 spins.

The light source wheel 220 and the optical filter wheel 230 may be plates, and the light source wheel 220 may be smaller in thickness than the optical filter wheel 230. Since the light source units 10 are attached to the light source wheel 220, the light source wheel 220 need not be thick. However, since the optical filter 250 is positioned inside the optical filter wheel 230, the optical filter wheel 230 may be thicker than the light source wheel 220.

The light source units 10 may be attached to the bottom end surface of the light source wheel 220. The optical filters 250 may be disposed in parallel with the optical filter wheel 230 between the top and bottom ends of the optical filter wheel 230.

The light source unit 10 and the optical filter 250 correspond to each other. The light source unit 10 and the optical filter 250 correspond to each other may mean that the light source unit 10 and the optical filter 250 are disposed in positions corresponding to each other or that the characteristics of the light source unit 10 correspond to the characteristics of the optical filter 250. The light source unit 10 and the optical filter 250 are disposed in processors corresponding to each other may mean that the light source unit 10 and the optical filter 250 are arranged along an excitation path so that the light emitted from the light source unit 10 passes through the optical filter 250. The characteristics of the light source unit 10 correspond to the characteristics of the optical filter 250 may mean that the characteristics of the light source unit 10 and the optical filter 250 are determined so that the light emitted from the light source unit 10 passes through the optical filter 250. Thus, the characteristics of the optical filter 250 are determined depending on the characteristics of the light source unit 10, and the optical filter 250 is disposed along the path of the light source unit 10. For example, if the first light source unit 10 emitting light of the first wavelength is disposed on the light source wheel 220, the first optical filter 250 transmitting light of the first wavelength is disposed on the path of the light emitted from the first light source unit 10.

FIG. 7 is a view illustrating a light irradiation process by rotation of a light source wheel 730. For ease of description, the light source wheel 730 is briefly shown. The light source wheel 730 includes four light source units 701 to 704. Although no reaction region is shown, the first reaction region includes a light irradiation region 711 and a light irradiation region 714. The second reaction region includes a light irradiation region 712 and a light irradiation region 713.

FIG. 7 illustrates a method in which four light sources 701 to 704 radiate light to four light irradiation regions 711 to 714 on two reaction regions while rotating. As the light source wheel 730 rotates, the positions of the light source units 701 to 704 are simultaneously changed. The light source wheel 730 may rotate clockwise or counter-clockwise.

Reaction may be performed in the first reaction region and second reaction region by independent protocols, and the first reaction region and the second reaction region may reach the light detection time individually or simultaneously.

If the two reaction regions both reach the detection time, the four light source units 701 to 704 may synchronously radiate light, and the four detectors 721 to 724 may synchronously detect light. As the four light source units 701 to 704 are rotated at 90 degrees to be simultaneously repositioned, the first light source unit 701 is positioned on the fourth light irradiation region 714, the second light source unit 702 on the first light irradiation region 711, the third light source unit 703 on the second light irradiation region 712, and the fourth light source unit 704 on the third light irradiation region 713. The repositioned light source units 701 to 704 radiate light to the light irradiation regions 711 to 714, and the detectors 721 to 724 detect light. In the same manner, the four light source units 701 to 704 are rotated by 90 degrees, sequentially radiating light to the light irradiation regions 711 to 714.

Each of the four detectors 721 to 724 corresponds to a respective one of the four light irradiation regions 711 to 714. Thus, one detector is able to detect the light emitted from one light irradiation region.

The first detection filter wheel 731 is disposed before the first and fourth detectors 721 and 724, and the second detection filter wheel 732 is disposed before the second and third detectors 723 and 724. The detection filter wheels 731 and 732 may rotate, switching the filters disposed before the detectors 721 to 724. The detection filter wheels 731 and 732 are synchronously rotated as the light source wheel 730 rotates. The filters positioned before the detector are determined depending on which light source is positioned on the light irradiation regions 711 to 714.

Where only one reaction region reaches the light detection time, the light source units positioned on the light irradiation region of the corresponding reaction region may radiate light while the light source units positioned on the light irradiation region of the other reaction region radiate no light. In this case, only the detector for the area irradiated with light may be controlled to detect light.

Where independent reaction regions are positioned adjacent to each other, and one reaction region has two light irradiation regions, use of the optical module in which the light source units are rotated allows for efficient light detection not only when two reaction regions individually reach the light detection time but also when the two reaction regions simultaneously reach the light detection time.

In the optical module of FIG. 7, the four light sources 701 to 704 may be rotated to radiate light to the four light irradiation regions 711 to 714 on the four reaction regions. Although no reaction region is shown, the first reaction region includes a light irradiation region 711. The second reaction region includes a light irradiation region 712. The third reaction region includes a light irradiation region 713. The fourth reaction region includes a light irradiation region 714. If the corresponding reaction region reaches the light detection time while the light source units rotate, the light source unit radiates light.

In the optical module of FIG. 7, the four light sources 701 to 704 may be rotated to radiate light to the two light irradiation regions 711 and 712 on the two reaction regions. The first reaction region includes a light irradiation region 711. The second reaction region includes a light irradiation region 712. No reaction region is present in the light irradiation region 713 and the light irradiation region 714.

Figure 8:
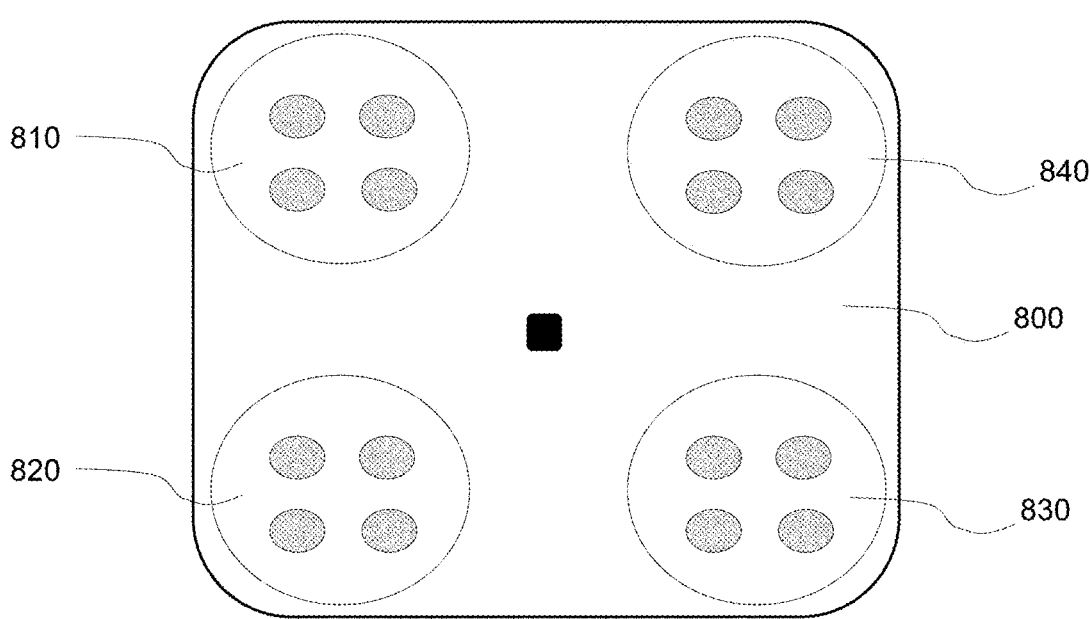
FIG. 8 is a view illustrating an example in which a light source wheel is divided into a plurality of regions.

FIG. 8 is a view illustrating an example in which a light source wheel 800 is divided into a plurality of regions. FIG. 8 illustrates an example in which the light source wheel 800 is divided into four light source units 810 to 840.

Although FIG. 8 illustrates an example in which four light sources are disposed in one light source unit, one or more light sources may be disposed in one light source unit.

According to an embodiment, when a plurality of light sources are arranged in one light source unit, they may be arranged symmetrically, particularly, point-symmetrically. According to an embodiment, where a plurality of light sources are arranged in one light source unit, the plurality of light sources are arranged radially.

In FIG. 8, when the light source wheel 800 includes four light source units 810 to 840, the light source wheel 800 may be shaped as a rectangle. Although the light source units 810 to 840 are shown as circular, the light source units 810 to 840 may not be independently shown in the light source wheel 800, and the light source units 810 to 840 may mean a group of light sources.

The light sources arranged in the same light source unit emit lights of the same wavelength. For example, in FIG. 8, the four light sources arranged in the first light source unit 810 emit lights of the first wavelength, the four light sources arranged in the second light source unit 820 emit lights of the second wavelength, the four light sources arranged in the third light source unit 830 emit lights of the third wavelength, and the four light sources arranged in the fourth light source unit 840 emit lights of the fourth wavelength.

Figure 9:
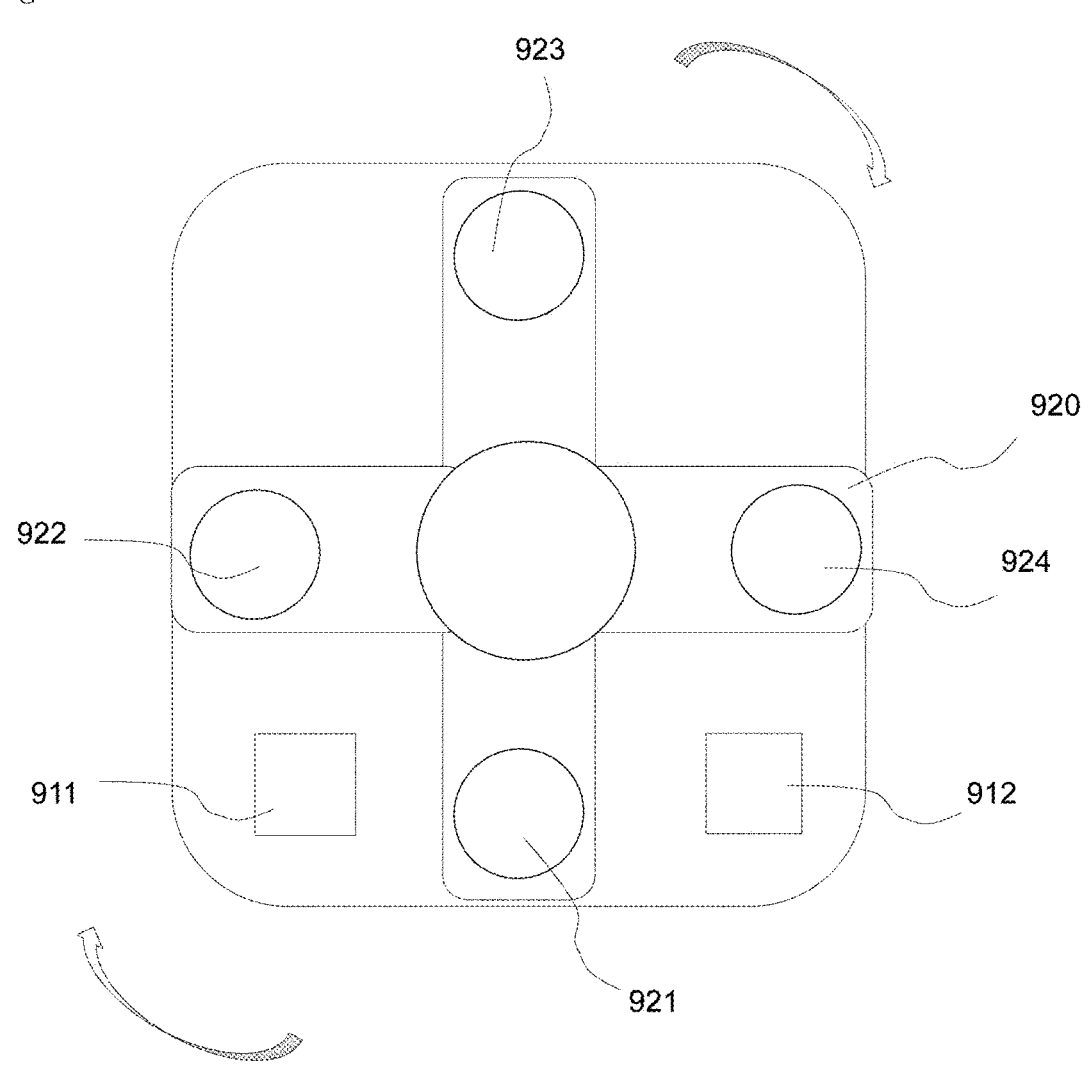
FIGS. 9 and 10 are views illustrating operations of a detection filter wheel disposed before detectors.
Figure 10:
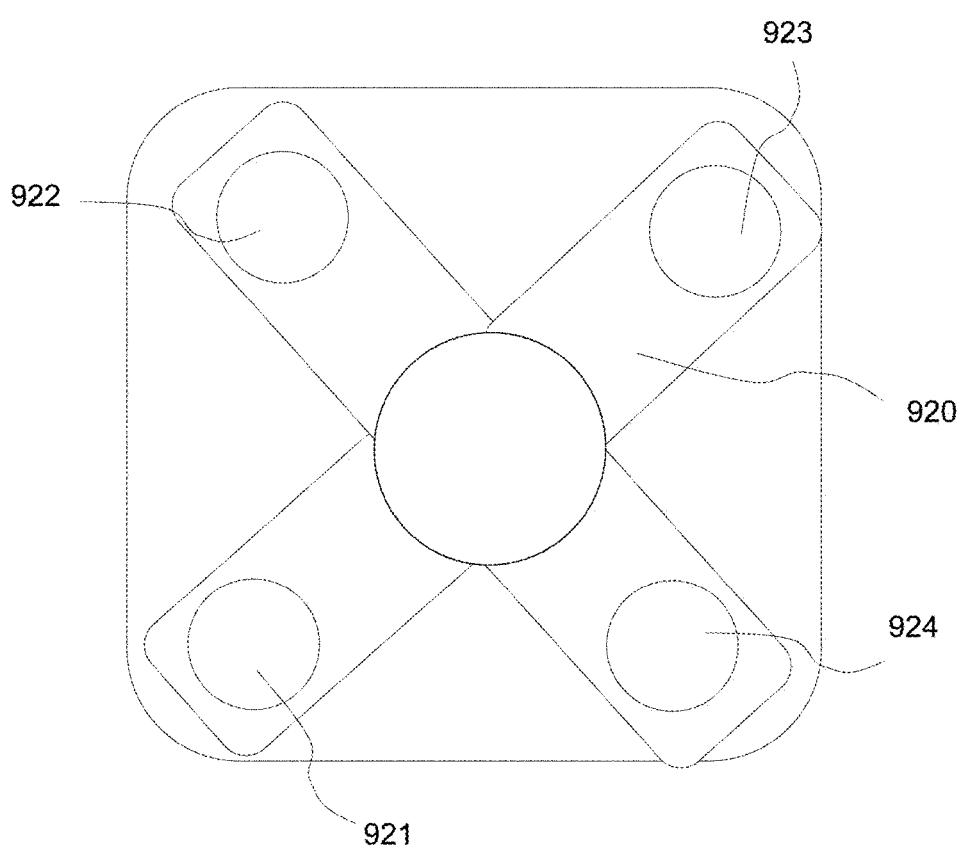

FIGS. 9 and 10 are views illustrating operations of a detection filter wheel 920 disposed before detectors 921 to 924. FIG. 9 illustrates an example in which the detection filter wheel 920 rotates, and FIG. 10 illustrates an example in which the detection filter wheel 920 stops, and the detection filters 921 to 924 are positioned before the detectors 911 and 912.

One detection filter wheel 920 is disposed before two detectors 911 and 912. The detection filter wheel 920 may be rotated before the detectors 911 and 912 by a motor. In an example, the detection filter wheel 920 may be rotated at 90 degrees at a time, and two of the four detection filters 921 to 924 may be disposed before the detectors 911 and 912. As the detection filter wheel 920 rotates, the detection filters 921 to 924 may simultaneously be repositioned. If the detection filters and filter wheel configured in this wayare included, the filter wheel including one detection filter set may be used for a plurality of detectors and, thus, the number of filters to be used for the entire light detection device may be reduced.

The detection filters 921 to 924 filter the light incident to the two detectors 911 and 912. The detection filters 921 to 924 may be bandpass filters. Thus, the detection filters 921 to 924 transmit light of a specific wavelength.

According to an embodiment, the light detection device may comprise a plurality of optical modules. According to an embodiment, when a plurality of optical modules are used, the reaction regions irradiated with light by the optical modules are configured not to cross each other. For example, where two optical modules are used, the reaction regions irradiated with light by one optical module differ from the reaction regions irradiated with light by the other optical module.

According to an embodiment, the light detection device according to the disclosure comprises two optical modules 200, three reaction regions 40, and three or six detectors 60. The optical modules 200 are rotational optical modules 200 each including four light source units 10 respectively disposed in the quadrants. The three reaction regions 40 are thermally independent from each other and each reaction region 40 includes 4×8 wells. According to an embodiment, one reaction region has two light irradiation regions. Light detection is performed on two reaction regions using one optical module 200, and light detection is performed on one reaction region using the other optical module 200.

Light sources disposed in a single light source unit may emit light of the same wavelength range. Such a light source unit is referred to as a single-wavelength light source unit. In addition, light sources disposed in a single light source unit may emit light of two or more wavelength ranges. Such a light source unit is referred to as a multi-wavelength light source unit. The terms "wavelength range"and "wavelength band"may have the same meaning and be interchangeably used herein.

According to an implementation of the present disclosure, the light module may comprise a multi-wavelength light source unit. According to an implementation of the present disclosure, one or more light source units among the plurality of light source units may be multi-wavelength light source units in each of which a first light source emitting light of a first wavelength range and a second light source emitting light of a second wavelength range different from the first wavelength range are disposed.

The single-wavelength light source unit is a light source unit that generates excitation light of a single specific wavelength range, while the multi-wavelength light source unit is a light source unit that generates excitation light of two or more different wavelength ranges. The multi-wavelength light source unit may selectively generate excitation light of two or more different specific wavelength ranges, thereby selectively exciting an intended optical label from among two or more different optical labels (e.g. a fluorescence labels) that may be included in the samples.

The light source unit may include one or more light sources that may be arrayed regularly. Accordingly, the above-described light source unit may uniformly radiate light to the area of an intended reaction region.

According to an implementation of the present disclosure, the first light source and the second light source may be arrayed regularly in a single light source unit of the light source wheel.

According to an implementation of the present disclosure, the multi-wavelength light source unit may further comprise a light source to generate light of a wavelength range different from those of the first light source and the second light source. The number of different wavelength ranges of excitation light that the multi-wavelength light source unit may selectively generate is not specifically limited. Particularly, the number of different wavelength ranges of excitation light may be in the range of 2 to 5, 2 to 4, or 2 and 3.

The multi-wavelength light source unit of the light module according to the present disclosure may sequentially apply power to the light sources of different wavelength ranges, thereby sequentially radiating light of different wavelength ranges. Thus, the light module according to the present disclosure may excite two or more labels using a single excitation light path without spatial movement of the light source unit itself or spatial movement of the light sources in the light source unit. In this case, the distribution of light for each wavelength region radiated to the reaction region is required to be the same. For example, the distribution of light radiated to the reaction region must be uniform in both a case in which light emitted by the light sources of the first wavelength range is radiated alone and a case in which light emitted by the light sources of the second wavelength range is radiated alone.

In this regard, the light sources of different wavelength ranges, included in the multi-wavelength light source unit, may be (1) provided on a common plane and (b) uniformly distributed.

In a case in which the wavelength range-specific light sources are arrayed regularly in the light source unit (e.g. the multi-wavelength light source unit) of the light source wheel, wavelength range-specific light generated by the light source unit may be radiated uniformly on the same area of the reaction region. Accordingly, it is possible to radiate light of different wavelength ranges to the reaction region without a spatial movement of the light source element or the light source wheel by supplying power or stopping the supply of power to the light sources of a specific wavelength range, thereby exciting two or more different optical labels.

According to an implementation of the present disclosure, the plurality of light sources included in the multi-wavelength light source unit may include the same number of wavelength range-specific light sources. For example, the number of the first light sources included in the multi-wavelength light source unit may be the same as the number of the second light sources included in the multi-wavelength light source unit.

According to an implementation of the present disclosure, the plurality of light sources included in the multi-wavelength light source unit may include different numbers of light sources according to the wavelength range. Even in the case in which the number of the first light sources differs from the number of the second light sources, the regular array of the wavelength range-specific light sources may allow excitation light to be uniformly radiated to the same area both when radiated by the first light source and when radiated by the second light source.

The number of the light sources of a specific wavelength range included in a single multi-wavelength light source unit may be, for example, 1, 2, 3, 4, 5, 6, 7, 8, 9, 10, 20, 30, 40, 50, 60, 70, 80, 90, 100, 200, 300, 400, or 500, independently of the other light sources of different wavelength ranges. The number of the first light sources or the second light sources may be, for example, 1 to 1,000, 1 to 500, 1 to 100, 1 to 50, 1 to 40, 1 to 30, 1 to 20, or 1 to 10.

According to an implementation of the present disclosure, the multi-wavelength light source unit is configured such that excitation light of the first wavelength range and excitation light of the second wavelength range are radiated to the same sample accommodated in the reaction region. Specifically, the multi-wavelength light source unit may be directed toward the reaction region such that the excitation light of the first wavelength range and the excitation light of the second wavelength range generated in the light source unit may directly arrive at the reaction region, or may be directed toward a reflector or an optical fiber such that the excitation light of the first wavelength range and the excitation light of the second wavelength range may arrive at the reaction region through the reflector or the optical fiber.

Since the multi-wavelength light source unit includes the first light source generating the excitation light of the first wavelength range and the second light source generating the excitation light of the second wavelength range, the excitation light of the first wavelength range and the excitation light of the second wavelength range may be selectively generated. The second wavelength range is a wavelength range different from the first wavelength range. Thus, the multi-wavelength light source unit may selectively excite two or more different optical labels. According to an implementation of the present disclosure, the first wavelength range comprises a wavelength range of light by which a first optical label may be excited, while the second wavelength range comprises a wavelength range of light by which a second optical label may be excited.

Each of the excitation light of the first wavelength range and the excitation light of the second wavelength range is a wavelength range of light by which a specific optical label may be excited. The optical label that may be excited by the excitation light of the first wavelength range or the excitation light of the second wavelength range may be an optical label selected from the group consisting of, but not limited to, Cy2™ YO-PRO™-1, YOYO™-1, Calcein, FITC, FluorX™, Alexa™, Rhodamine 110, Oregon Green™ 500, Oregon Green™ 488, RiboGreen™, Rhodamine Green™ Rhodamine 123, Magnesium Green™, Calcium Green™, TO-PRO™-1, TOTO1, JOE, BODIPY530/550, DiI, BODIPY TMR, BODIPY558/568, BODIPY564/570, Cy3™ Alexa™ 546, TRITC, Magnesium Orange™, Phycoerythrin R&B, Rhodamine Phalloidin, Calcium Orange™, Pyronin Y, Rhodamine B, TAMRA, Rhodamine Red™, Cy3.5™, ROX, Calcium Crimson™, Alexa™ 594, Texas Red, Nile Red, YO-PRO™-3, YOYO™-3, R-phycocyanin, C-Phycocyanin, TO-PRO™-3, TOTO3, DiD DilC(5), Cy5™, Thiadicarbocyanine, Cy5.5, HEX, TET, Biosearch Blue, CAL Fluor Gold 540, CAL Fluor Orange 560, CAL Fluor Red 590, CAL Fluor Red 610, CAL Fluor Red 635, FAM, Fluorescein, Fluorescein-C3, Pulsar 650, Quasar 570, Quasar 670, and Quasar 705. In particular, the optical label that may be excited by the excitation light of the first wavelength range or the excitation light of the second wavelength range may be an optical label selected from the group consisting of, but not limited to, FAM, CAL Fluor Red 610, HEX, Quasar 670, and Quasar 705.

According to the present disclosure, the excitation light of the second wavelength range generated by the second light source included in a single multi-wavelength light source unit is required to not excite an optical label excited by the excitation light of the first wavelength range, from among the optical labels included in the sample, while the excitation light of the first wavelength range generated by the first light source is required to not excite an optical label excited by the excitation light of the second wavelength range, from among the optical labels included in the sample. In this regard, the wavelength range of light generated by the first light source may be spaced apart from the wavelength range of light generated by the second light source. Specifically, the peak wavelength of the first light source may be spaced apart from the peak wavelength of the second light source by a predetermined magnitude. The peak wavelength means a wavelength having a highest light intensity from among spectra of light generated by the light source. According to an implementation of the present disclosure, the peak wavelength of the first light source may be spaced apart from the peak wavelength of the second light source by a range of from 50 nm to 500 nm, 60 nm to 300 nm, or 70 nm to 200 nm.

In addition, according to an implementation of the present disclosure, one or more filter areas from among the plurality of filter areas of the light module according to the present disclosure may comprise a multi bandpass filter including a first passband and a second passband.

According to the present disclosure, the bandpass filter is a filter that selectively allows light in a specific wavelength range to pass therethrough. The wavelength range of light passing through each of the bandpass filters is referred to as the passband of the filter. The passband may be indicated on the basis of the wavelength range. A filter including a specific passband is a filter that allows a light of wavelength included in the specific passband to pass therethrough. A filter having a single passband is referred to as a single bandpass filter. Thus, the single bandpass filter selectively allows light in a single wavelength range to pass therethrough.

A filter having two or more passbands is referred to as a multi bandpass filter. That is, the multi bandpass filter selectively allows light in two or more wavelength ranges to pass therethrough. Here, the two or more passbands do not overlap each other. The number of passbands included in the multi bandpass filter may be in the range of from 2 to 5, from 2 to 4, or 2 and 3.

The number of the passbands included in the multi bandpass filter may be the same as the number of different wavelength ranges of excitation light selectively generated by the multi-wavelength light source unit. The passbands included in the multi bandpass filter are formed such that different wavelength ranges of excitation light generated by the multi-wavelength light source unit may pass through the multi bandpass filter.

The multi bandpass filter according to the present disclosure includes a first passband and a second passband. That is, the multi bandpass filter according to the present disclosure may allow light corresponding to the first passband or the second passband to pass therethrough. According to an implementation of the present disclosure, the first passband includes the first wavelength range, while the second passband includes the second wavelength range. The first passband including the first wavelength range means that the multi bandpass filter including the first passband allows light, generated by a light source that generates light of the first wavelength range, to pass therethrough. The first wavelength range means the wavelength range of light generated by the first light source of the multi-wavelength light source unit, while the second wavelength range means the wavelength range of light generated by the second light source of the multi-wavelength light source unit.

Specifically, the first passband including the first wavelength range means that the multi bandpass filter including the first passband allows the entirety or a portion of the wavelength range of light, generated by the light source generating light of the first wavelength range, to pass therethrough. Thus, the passband of the multi bandpass filter including the wavelength range of light generated by the light source means that the wavelength range of the passband includes the entirety or a portion of the wavelength range of light generated by the light source. For example, in the passband of the multi bandpass filter including the wavelength range of the light source generating light of a wavelength range of from 450 nm to 650 nm, the minimum wavelength of the passband is shorter than 650 nm, the maximum wavelength of the passband is longer than 450 nm, and the maximum wavelength is longer than the minimum wavelength. According to an implementation of the present disclosure, the first passband may include the entirety or a portion of the first wavelength range, while the second passband may include the entirety or a portion of the second wavelength range. The entirety or a portion of light of the first wavelength range, generated by the first light source, passes through the first passband to be irradiated to the sample accommodated in the reaction region, while the entirety or a portion of light of the second wavelength range, generated by the second light source, passes through the second passband to be irradiated to the sample accommodated in the reaction region. The minimum wavelength and the maximum wavelength of the passband are wavelengths obtaining a specific ratio of transmittance with respect to the highest transmittance of the multi bandpass filter. For example, the specific ratio may be 10%, 20%, 30%, 40%, or 50%. In particular, the specific ratio may be 50%.

According to an implementation of the present disclosure, the first passband and the second passband may not overlap each other. Specifically, both the maximum wavelength and the minimum wavelength of the first passband may be shorter than the minimum wavelength of the second passband or longer than the maximum wavelength of the second passband.

Each of the first passband and the second passband may include a wavelength range of light that may excite a specific optical label. Specific types of the optical label are as described hereinbefore. In particular, the optical label may be an optical label selected from the group consisting of, but not limited to, FAM, CAL Fluor Red 610, HEX, Quasar 670, and Quasar 705.

Excitation light passing through the second passband included in a single multi bandpass filter according to the present disclosure is required to not excite an optical label excited by the excitation light passing through the first passband, from among the optical labels included in the sample. In this regard, the wavelength range of the first passband may be spaced apart from the wavelength range of the second passband. Specifically, the central wavelength (CWL) of the first light source may be spaced apart from the central wavelength of the second light source by a predetermined magnitude. The central wavelength is a wavelength corresponding to a mid-point of the minimum wavelength and the maximum wavelength of the corresponding passband. According to an implementation of the present disclosure, the central wavelength of the first passband may be spaced apart from the central wavelength of the first passband by at least 10 nm, 20 nm, 30 nm, 40 nm, 50 nm, 60 nm, or 70 nm. According to an implementation of the present disclosure, the central wavelength of the first passband may be spaced apart from the central wavelength of the second passband by a range of from 10 nm to 500 nm, 20 nm to 400 nm, 30 nm to 300 nm, 30 nm to 200 nm, 50 nm to 200 nm, 60 nm to 200 nm, or 70 nm to 200 nm.

From among the optical labels used to detect a target analyte, in particular, a target nucleic acid, FAM and CAL Fluor Red 610 are suitable for selective excitation through a single light source unit, since absorption wavelengths thereof are spaced apart from each other. Thus, according to an implementation of the present disclosure, each of the first passband and the second passband may include the wavelength range of light that may excite FAM and CAL Fluor Red 610. Specifically, the central wavelength of the first passband may range from 450 nm to 500 nm, and the central wavelength of the second passband may range from 550 nm to 600 nm.

In a case in which the multi-wavelength light source unit is used alone, unnecessary wavelength ranges of light may not be precisely blocked according to the type of light sources used. In addition, it is impossible to obtain effects intended in the present disclosure by combining the multi bandpass filter to a white light source typically used in the conventional device to detect a target nucleic acid. According to the present disclosure, it is possible to selectively excite two or more optical labels using a combination of single light source unit-filter areas by combining the multi-wavelength light source unit capable of selectively generating excitation light of a specific wavelength range and the multi bandpass filter additionally limiting the wavelength range of the excitation light generated by the multi-wavelength light source unit.

According to an implementation of the present disclosure, the detection module may comprise the multi bandpass filter.

Specifically, the multi bandpass filter of the detection module may include the third passband and the fourth passband. That is, the multi bandpass filter of the detection module according to the present disclosure may allow light corresponding to the third passband and the fourth passband to pass therethrough. The third passband includes a wavelength range through which emission light of the optical label excited by excitation light of the first wavelength range passes, while the fourth passband includes a wavelength range through which emission light of the optical label excited by excitation light of the second wavelength range passes. Thus, according to an implementation of the present disclosure, the third passband may include the wavelength range of emission light emitted by the optical label that may be excited by excitation light passing through the first passband, while the fourth passband may include the wavelength range of emission light emitted by the optical label that may be excited by excitation light passing through the second passband.

Specifically, the third passband may include the entirety or a portion of the wavelength range of emission light emitted by the optical label that may be excited by excitation light passing through the first passband, while the fourth passband may include the entirety or a portion of the wavelength range of emission light emitted by the optical label that may be excited by excitation light passing through the second passband.

According to an implementation of the present disclosure, the passband of the multi bandpass filter of the light module and the passband of the multi bandpass filter of the detection module are not determined independently of each other. The multi bandpass filter of the light module has the passband including the wavelength range of excitation light of an optical label to be detected, while the multi bandpass filter of the detection module has the passband including the wavelength range of emission light of the same optical label. Accordingly, the relationship between the passbands of the two multi bandpass filters may be determined such that each of the passbands includes the wavelength range of excitation light of a optical label to be detected and the wavelength range of emission light emitted from the optical label.

According to an implementation of the present disclosure, the third passband and the fourth passband of the multi bandpass filter of the detection module may not overlap each other. Specifically, both the maximum wavelength and the minimum wavelength of the third passband may be shorter than the minimum wavelength of the fourth passband or may be longer than the maximum wavelength of the fourth passband.

Each of the third passband and the fourth passband may include the wavelength range of emission light emitted by a specific optical label. Specific types of the optical label are as described hereinbefore. In particular, the optical label may be an optical label selected from the group consisting of, but not limited to, FAM, CAL Fluor Red 610, HEX, Quasar 670, and Quasar 705.

The fourth passband included in the single multi bandpass filter according to the present disclosure is required to have a structure that prevents emission light of an optical label that emits light passing through the third passband, from among the optical labels included in the sample, from passing through the fourth passband. In this regard, the wavelength range of the third passband and the wavelength range of the fourth passband may be spaced apart from each other. Specifically, the central wavelength (CWL) of the third passband and the central wavelength of the fourth passband may be spaced apart from each other by a predetermined magnitude. According to an implementation of the present disclosure, the central wavelength of the third passband and the central wavelength of the fourth passband may be spaced apart from each other by at least 10 nm, 20 nm, 30 nm, 40 nm, 50 nm, 60 nm, or 70 nm. According to an implementation of the present disclosure, the central wavelength of the third passband and the central wavelength of the fourth passband may be spaced apart from each other by a range of from 10 nm to 500 nm, 20 nm to 400 nm, 30 nm to 300 nm, 30 nm to 200 nm, 50 nm to 200 nm, 60 nm to 200 nm, or 70 nm to 200 nm.

For example, from among the optical labels used to detect a target nucleic acid, FAM and CAL Fluor Red 610 are suitable for selective excitation through a single detection module, since absorption wavelengths thereof are spaced apart from each other. Thus, according to an implementation of the present disclosure, each of the third passband and the fourth passband may include the wavelength ranges of light emitted by FAM and CAL Fluor Red 610. Specifically, the central wavelength of the third passband may range from 500 nm to 550 nm, and the central wavelength of the fourth passband may range from 600 nm to 670 nm.

The positions of the light source units 210 and the bandpass filters 220 of the light module are moved by the motor 250 serving as the light module moving means, and excitation light of a variety of wavelength ranges is radiated to the reaction region. Synchronizedly, the positions of the detection filters 320 are moved by the motor 250 serving as the light module moving means, so that the detection filters 320 selectively allow the emission light in the variety of wavelength ranges generated by the excitation light to pass therethrough.

Accordingly, the number and type of the plurality of detection filters 320 of the detection module 300 may vary depending on the number and type of the bandpass filters 220 of the light module 200. Specifically, in the device according to the present disclosure, in a case in which the multi bandpass filter or the single bandpass filter is added to the light module 200, a multi bandpass filter or a single bandpass filter corresponding thereto may be added to the detection module 300. For example, in a case in which a single bandpass filter allowing light capable of exciting an optical label HEX to pass therethrough is added to the light module, a single bandpass filter allowing emission light of HEX to pass therethrough may be added to the detection module. In this case, a single bandpass filter including a passband of a central wavelength ranging from 510 nm to 560 nm may be used in the light module, and a single bandpass filter including a passband of a central wavelength ranging from 570 nm to 620 nm may be used in the detection module, in consideration of the emission light wavelength range of HEX. In another example, in a case in which a multi bandpass filter allowing excitation light capable to exciting optical labels HEX and Quasar 705 to pass therethrough is added to the light module, a multi bandpass filter allowing emission light of HEX and Quasar 705 to pass therethrough may be added to the detection module. In this case, a multi bandpass filter including both a passband of a central wavelength ranging from 510 nm to 560 nm and a passband of a central wavelength ranging from 640 nm to 680 nm may be used in the light module, and a multi bandpass filter including both a passband of a central wavelength ranging from 570 nm to 610 nm and a passband of a central wavelength ranging from 710 nm to 750 nm may be used in the detection module, in consideration of the emission light wavelength ranges of HEX and Quasar 705.

According to another aspect of the present disclosure, the present disclosure provides a computer-readable storage medium containing instructions stored therein, wherein when the instructions is executed by a computer, the instructions are configured to enable a processor of the computer to perform a method for detecting light, the method comprising: independently controlling temperatures of thermally independent reaction regions, wherein the reaction regions are capable of receiving one or more samples; positioning light source units in reaction regions reaching a light detection time among the reaction regions and irradiating the reaction regions with light, wherein the light source units are configured to be movable and comprising two or more light source units radiating different lights, and each of the light source units irradiate an area of predetermined size with light; and detecting light emitted from the reaction regions.

When the program instructions are executed by the processor, the program instructions are configured to enable a processor of the computer to perform the above method. The program instructions for performing the method for detecting light may include: (i) instructions for independently controlling temperatures of thermally independent reaction regions; (ii) instructions for positioning light source units in reaction regions reaching a light detection time among the reaction regions and irradiating the reaction regions with light; wherein the light source units are configured to be movable and comprising two or more light source units radiating different lights, and each of the light source units irradiate an area of predetermined size with light; and (iii) detecting light emitted from the reaction regions.

The method of the present disclosure is implemented by the processor. The processor may be embodied as a processor in a stand-alone computer or a processor in a network attached computer. The computer-readable storage medium may include any one of a variety of storage media known in the art such as CD-R, CD-ROM, DVD, flash memory, floppy disk, hard drive, portable HDD, USB, magnetic tape, MINIDISC, non-volatile memory card, EEPROM, optical disk, optical storage media, RAM, ROM, system memory, and web servers, but may not be limited thereto.

The instructions that implement the processor that executes the present disclosure may be included in the logic system. The instructions may be stored on a software recording medium (e.g., a portable HDD, a USB, a floppy disk, a CD and a DVD). Alternatively, the instructions may be downloadable or may be stored in a memory module (e.g., another memory such as a hard drive or local or attached RAM or ROM). The computer code executing the present disclosure may also be implemented in a variety of coding languages such as C, C++, Java, Visual Basic, VBScript, JavaScript, Perl, XML, Python, Bash and Nextfolw. Further, various languages and protocols may be used for external and internal storage and delivery of data sets and commands according to the present disclosure.

According to another aspect of the present disclosure, the present disclosure provides a device for detecting light, the device comprising: (a) a computer processor; and (b) the computer-readable storage medium of the present disclosure coupled to the processor.

According to one embodiment of the present disclosure, the device of the present disclosure may additionally include an input device that may receive, from the user, protocols for performing a light detection reaction for the sample, and a data providing device that may provide the user with the result of light detection of the sample. The data providing device includes an output device, a display device, a storage medium connection or recording device, and a network device capable of transmitting data in a wired or wireless manner.

The computer processor may be configured so that one processor performs all of the above-mentioned performance. Alternatively, the processor unit may be configured to allow each of multiple processors to perform each performance.

The storage medium, device and computer program in accordance with the present disclosure may be configured to implement the above-described method of the present disclosure on a computer. The overlapping content between the storage medium, device and computer program will be omitted in order to avoid the excessive complexity of the present disclosure.

While embodiments of the disclosure have been described above, it will be easily appreciated by one of ordinary skill in the art that the scope of the disclosure is not limited thereto. Thus, the scope of the disclosure is defined by the appended claims and equivalents thereof.

The invention claimed is:

1. A light detection device, comprising:
thermally independent reaction regions, wherein the reaction regions are capable of receiving one or more samples, and wherein temperatures of the reaction regions are controlled independently;
light source units irradiating the reaction regions with light, wherein the light source units comprise two or more light source units radiating different lights, and wherein each of the light source units is configured to irradiate an area of predetermined size with light, and wherein the light source units are configured to be movable;
one or more controllers controlling the temperatures of the reaction regions independently and controlling movement of the light source units; and
detectors detecting light emitted from the reaction regions,
wherein the light source units are arranged around a rotational axis, and wherein as the light source units are rotated around the rotational axis, the areas of predetermined size irradiated with the light by the light source units are changed.

2. The light detection device according to claim 1, wherein each of the reaction regions comprises wells arranged in an n×m matrix, and wherein n or m is a natural number which is two or more.

3. The light detection device according to claim 1, wherein one of the light source units irradiates one entire reaction region with the light, or two or more light source units separately irradiate one entire reaction region with the light.

4. The light detection device according to claim 3, wherein two of the light source units separately irradiate one entire reaction region with the light by dividing the one entire reaction region.

5. The light detection device according to claim 1, wherein the light source units are simultaneously moved, and wherein areas irradiated with the light by the light source units are simultaneously changed.

6. The light detection device according to claim 1, wherein the light source units are rotated around the rotational axis at 90 degrees, 180 degrees, 270 degrees, or 360 degrees.

7. The light detection device according to claim 1, wherein at least one of the light source units is positioned in one reaction region, and at least one other light source unit is positioned in another reaction region so that different reaction regions may be synchronously irradiated with different lights.

8. The light detection device according to claim 1, wherein each of the light source units comprises one or more light sources.

9. The light detection device according to claim 1, wherein the light source units comprise four or more light source units capable of radiating four or more different lights.

10. The light detection device according to claim 1, wherein the reaction regions comprise a first reaction region and a second reaction region, wherein the light source units comprise a first light source unit and a second light source unit, and wherein when the first reaction region and the second reaction region simultaneously reach a light detection time, as the light source units are rotated, the first light source unit is positioned in the first reaction region, and the second light source unit is positioned in the second reaction region to synchronously irradiate different areas with different lights.

11. The light detection device according to claim 1, wherein one or more different detectors of the detectors are assigned to each of the reaction regions, and wherein light emitted from each reaction region is measured by the one or more different detectors assigned.

12. The light detection device according to claim 1, wherein the controller independently controls on/off of light irradiation of the light source units.

* * * * *